United States Patent
Germain et al.

(10) Patent No.: US 10,806,516 B2
(45) Date of Patent: Oct. 20, 2020

(54) VIRTUAL 4D STENT IMPLANTATION PATH ASSESSMENT

(71) Applicant: General Electric Company, Schnectady, NY (US)

(72) Inventors: Sylvain Germain, Buc (FR); Jerome Bausse, Buc (FR)

(73) Assignee: General Electric Company, Schenectady, NY (US)

( * ) Notice: Subject to any disclaimer, the term of this patent is extended or adjusted under 35 U.S.C. 154(b) by 774 days.

(21) Appl. No.: 15/186,951

(22) Filed: Jun. 20, 2016

(65) Prior Publication Data
US 2017/0360508 A1 Dec. 21, 2017

(51) Int. Cl.
*A61B 34/10* (2016.01)
*G16H 50/50* (2018.01)
*A61F 2/95* (2013.01)

(52) U.S. Cl.
CPC .............. *A61B 34/10* (2016.02); *G16H 50/50* (2018.01); *A61B 2034/107* (2016.02); *A61F 2/95* (2013.01)

(58) Field of Classification Search
CPC ... A61B 34/10; A61B 2034/107; G06F 19/00; G16H 50/50; A61F 2/95
See application file for complete search history.

(56) References Cited

U.S. PATENT DOCUMENTS

| | | | | |
|---|---|---|---|---|
| 8,922,552 | B2* | 12/2014 | Rouet et al. | 345/420 |
| 2009/0088830 | A1* | 4/2009 | Mohamed | A61F 2/91 623/1.11 |
| 2014/0254906 | A1 | 9/2014 | Polle et al. | |
| 2014/0257763 | A1* | 9/2014 | Fang | G06F 17/50 703/1 |
| 2015/0049081 | A1* | 2/2015 | Coffey | G06T 19/006 345/419 |
| 2015/0320324 | A1 | 11/2015 | Jung et al. | |
| 2015/0366628 | A1* | 12/2015 | Ingmanson | A61B 5/015 600/424 |
| 2016/0022208 | A1* | 1/2016 | Gopinath | A61B 5/02007 600/427 |

(Continued)

FOREIGN PATENT DOCUMENTS

| | | |
|---|---|---|
| EP | 2712553 A2 | 4/2014 |
| WO | 2015089013 A1 | 6/2015 |
| WO | WO-2015089013 A1 * | 6/2015 ........... A61B 5/6852 |

OTHER PUBLICATIONS

International Search Report and Written Opinion for corresponding PCT Application PCT/US2017/036952 dated Aug. 9, 2017; 13 pages.

*Primary Examiner* — Eliza A Lam
(74) *Attorney, Agent, or Firm* — Amin, Turocy & Watson, LLP

(57) ABSTRACT

Systems and techniques for virtual assessment of an implantation path for a medical device are presented. A system can analyze multi-dimensional medical imaging data regarding a patient body and a lesion area, generate a set of paths to reach the lesion area for deployment of a medical device, rank the set of paths to reach the lesion area, and recommend a subset of the paths for deployment of the medical device. The system can also generate a display of the recommendations and a multi-dimensional visualization of the recommended subset of paths for the deployment of the medical device.

20 Claims, 16 Drawing Sheets

(56) References Cited

U.S. PATENT DOCUMENTS

2016/0217375 A1* 7/2016 Choi ................. G06F 19/00
2016/0256610 A1* 9/2016 Zhou ................. A61L 31/06
2017/0065349 A1* 3/2017 Ourselin ............ G06F 30/00

* cited by examiner

VIRTUAL 4D STENT IMPLANTATION PATH ASSESSMENT

BACKGROUND

Thousands of medical procedures are performed every day, and a stent is often employed during theses medical procedures. A stent is a tube (e.g., a plastic tube, a metal tube, or a mesh tube) that is inserted into an anatomic vessel (e.g., an artery, etc.) to keep a passageway of the anatomic vessel open. Conventional stent implantation procedures involve human interpretation of medical imaging data to determine a stent implantation path. However, such conventional stent implantation procedures are generally inefficient and/or prone to inaccuracies. Furthermore, these stent implantation procedures can be invasive to a patient body and/or can cause damage to an anatomic vessel.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

In accordance with non-limiting implementation, a system includes a path assessment component, a recommendation component, and a visualization component. The path assessment component analyzes multi-dimensional medical imaging data regarding a patient body and a lesion area. The path assessment component generates a set of paths to reach the lesion area for deployment of a medical device. The recommendation component ranks the set of paths to reach the lesion area. The recommendation component recommends a subset of the paths for deployment of the medical device. The visualization component generates a display of the recommendations and a multi-dimensional visualization of the recommended subset of paths for the deployment of the medical device.

Additionally, a non-limiting implementation provides for analyzing multi-dimensional medical imaging data associated with a patient body and a lesion area associated with an anatomic vessel, generating a set of implantation paths for a medical device to reach the lesion area, ranking the implantation paths for the medical device to reach the lesion area, recommending a subset of the implantation paths for deployment of the medical device, and generating a display associated with a multi-dimensional visualization of the recommended subset of implantation paths for the deployment of the medical device.

In accordance with another non-limiting implementation, a computer readable storage device comprising instructions that, in response to execution, cause a system comprising a processor to perform operations, comprising: segmenting three-dimensional medical imaging data associated with an anatomic vessel and a lesion area associated with the anatomic vessel, generating a set of candidate implantation paths for a medical device to reach the lesion area, ranking the candidate implantation paths for the medical device to reach the lesion area, selecting an implantation path for deployment of the medical device based on the ranking, and generating a display associated with a three-dimensional rendering of the implantation path for the deployment of the medical device.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
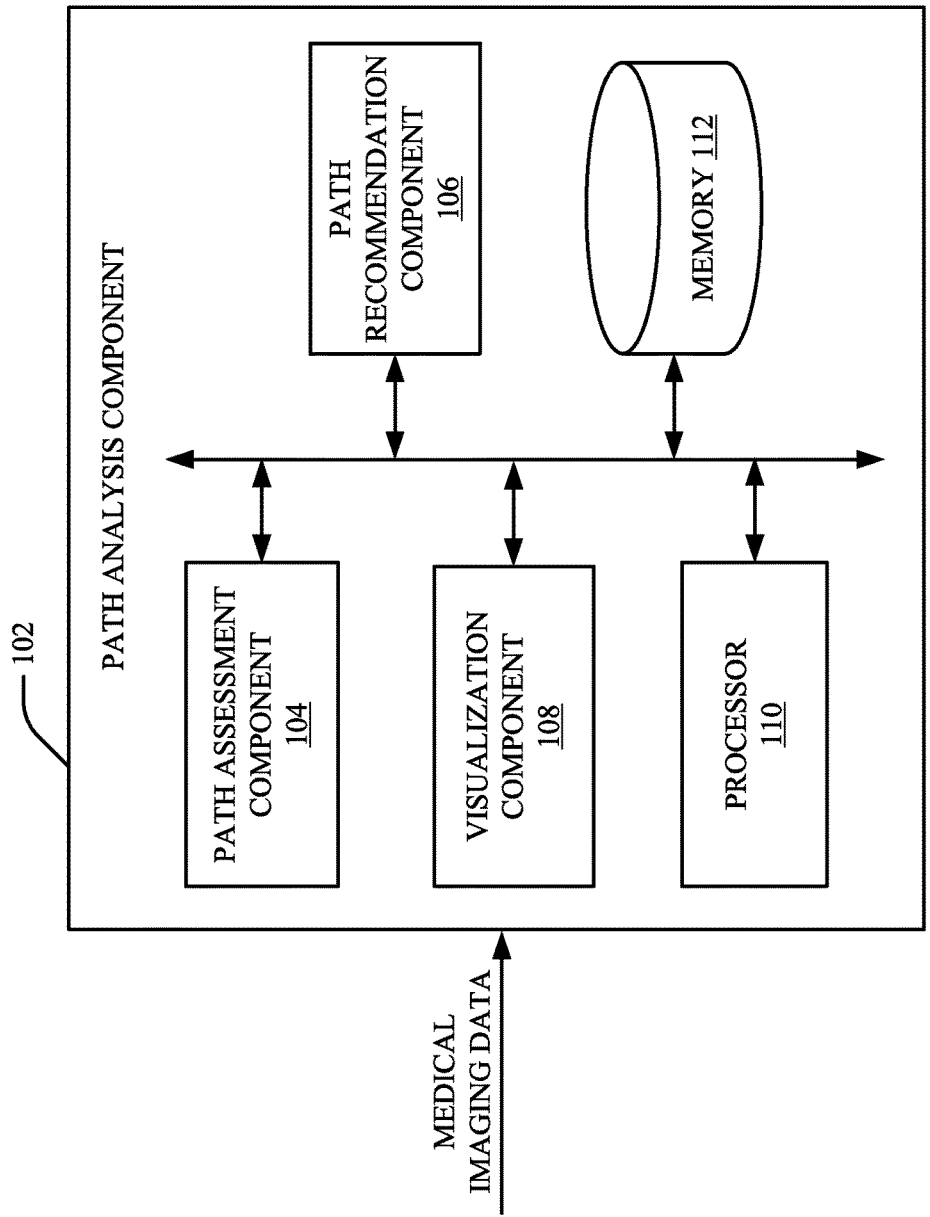
FIGS. 1-7 illustrate a high-level block diagram of an example pattern detection component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for virtually determining and/or assessing an implantation path for a medical device are presented. For example, as compared to conventional implantation procedures for a medical device that involve human interpretation of two-dimensional (2D) medical imaging data and/or human trial and error with respect to a physical anatomic vessel, the subject innovations provide for virtual selection and/or virtual assessment of an implantation path (e.g., an access path) for a medical device to traverse an anatomic vessel to a deployment area (e.g., a lesion area) associated with the anatomic vessel. The medical device can be a stent (e.g., a vascular stent) or another type of implantable medical device employed during a medical procedure associated with the anatomic vessel. To facilitate determination of an implantation path for the medical device, a three-dimensional (3D) anatomical model (e.g., a patient-specific 3D anatomical model) of the deployment area (e.g., the lesion area) and/or the anatomic vessel can be generated from 3D medical imaging data. Furthermore, a list of candidate implantations paths to reach the deployment area associated with the anatomic vessel can be generated. The list of candidate implantation paths can be generated and/or ranked based on a score determined for each candidate implantation path included in the list of candidate implantation paths.

To assess accessibility of the deployment area associated with the anatomic vessel, properties (e.g., mechanical properties and/or physical properties) associated with the medical device and/or properties (e.g., mechanical properties and/or physical properties) associated with the anatomic vessel can be employed. By employing these properties of the medical device and/or the anatomic vessel, an implantation path to the deployment area associated with the anatomic vessel can be virtually explored in 3D. For example, a display of a user device can be provided with a 3D visualization sequence portraying progress of the medical device along the anatomic vessel. Furthermore, selection of the medical device for the implantation path can be assessed. Moreover, capabilities of the anatomic vessel and/or the medical device can allow automatic selection of the medical device and/or the implantation path. For instance, a recommended implantation path from the list of candidate implantation paths and/or a recommended medical device can be determined based on a result of all candidate implantation path assessments. As such, a medical procedure for implanting a medical device into an anatomic vessel can be more efficient and/or more accurate. Furthermore, invasive procedures and/or damage to an anatomic vessel can be minimized by replacing human trial and error for implanting a medical device into an anatomic vessel.

Referring initially to FIG. 1, there is illustrated an example system 100 that determines and/or assesses an implantation path for a medical device, according to an aspect of the subject disclosure. The system 100 can be employed by various systems, such as, but not limited to medical device systems, medical imaging systems, medical modeling systems, simulation systems, medical device navigation systems, stent navigation systems, enterprise imaging solution systems, advanced diagnostic tool systems, image management platform systems, care delivery management systems, artificial intelligence systems, machine learning systems, neural network systems, and the like. In one example, the system 100 can be associated with a volume viewer system to facilitate visualization and/or interpretation of medical imaging data. Moreover, the system 100 and/or the components of the system 100 can be employed to use hardware and/or software to solve problems that are highly technical in nature (e.g., related to processing 3D data, related to medical modeling, related to medical imaging, related to artificial intelligence, etc.), that are not abstract and that cannot be performed as a set of mental acts by a human.

The system 100 can include a path analysis component 102 that can include a path assessment component 104, a path recommendation component 106 and a visualization component 108. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the path analysis component 102) can include memory 112 for storing computer executable components and instructions. The system 100 (e.g., the path analysis component 102) can further include a processor 110 to facilitate operation of the instructions (e.g., computer executable components and instructions) by the system 100 (e.g., the path analysis component 102).

The path analysis component 102 can perform analysis for determining and/or assessing an implantation path for a medical device. The medical device can be an implantable medical device. For example, the medical device can be a stent such as a vascular stent or another type of stent. In another example, the medical device can be a catheter. In yet another example, the medical device can be another type of implantable medical device. The path analysis component 102 (e.g., the path assessment component 104) can receive medical imaging data (e.g., MEDICAL IMAGING DATA shown in FIG. 1). The medical imaging data can be multi-dimensional medical imaging data (e.g., 3D medical imaging data) associated with one or more medical imaging devices. For instance, the medical imaging data can be a set of consecutive images and/or a set of data that is repeatedly captured via a set of sensors (e.g., a set of sensors associated with a medical imaging device) during an interval of time. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, a computed tomography (CT) device, a magnetic resonance imaging (MRI) device, a positron emission tomography (PET) device, a computed axial tomography (CAT) device, an ultrasound device, another type of medical imaging device, etc.

In an aspect, the medical imaging data can be rendered from 2D images. For example, the medical imaging data can be rendered into 3D medical imaging data from 2D medical imaging data (e.g., 2D CT imaging data, 2D MRI imaging data, etc.). Additionally or alternatively, the medical imaging data (e.g., the multi-dimensional mesh model) can be generated based on one or more 3D sensor associated with one or more 3D imaging devices. The medical imaging data can be associated with a multi-dimensional mesh model (e.g., a 3D mesh model). For instance, the medical imaging data can be associated with a 3D surface model constructed from polygons, vectors, vertices, edges and/or faces. The medical imaging data can also provide a mapping of a patient body (e.g., anatomical structure(s) of a patient body) and/or a lesion area of a patient body.

The path assessment component 104 can analyze the medical imaging data. By analyzing the medical imaging data, the path assessment component 104 can generate a set of implantation paths (e.g., a set of candidate implantation paths) to reach the lesion area for deployment of the medical device. An implantation path from the set of implantation paths can be an implantation path, through an anatomic vessel of the patient body, for the medical device. For instance, an implantation path from the set of implantation paths can be a route for the medical device to reach the lesion area of the patient body via the anatomic vessel. In a non-limiting example, an implantation path from the set of implantation paths can be a stent implantation path.

The path assessment component 104 can analyze the medical imaging data by segmenting the medical imaging data. Segmentation of the medical imaging data can involve identification and/or separation of data chunks associated with the medical imaging data. Segmentation of the medical imaging data can also be performed to define the lesion area and/or the anatomic vessel. For example, the path assessment component 104 can segment a portion of the medical imaging data associated with the lesion area and/or a portion of the medical imaging data associated with the anatomic vessel. One or more segmentation algorithms can be employed by the path assessment component 104 to segment the medical imaging data. The path assessment component 104 can perform segmentation based on geometric information and/or texture information associated with the medical imaging data. The path assessment component 104 can also analyze mesh data associated with the medical imaging data to facilitate segmentation of the medical imaging data.

In an embodiment, the path assessment component 104 can segment the medical imaging data based on a 3D edge detection technique. For example, the path assessment component 104 can detect edges associated with the medical imaging data to determine regions of the medical imaging data that are associated with the lesion area and/or the anatomical vessel. The path assessment component 104 can segment the medical imaging data based on a classification technique. For example, the path assessment component 104 can employ pattern recognition to classify portions of the medical imaging data that are associated with the lesion area and/or the anatomical vessel. Additionally or alternatively, the path assessment component 104 can segment the medical imaging data based on a clustering technique. For example, the path assessment component 104 can group portions of the medical imaging data based on similarities and/or matching to facilitate identification of medical imaging data associated with the lesion area and/or the anatomical vessel.

The path assessment component 104 can divide the medical imaging data into one or more data chunks based on content type and/or features associated with the medical imaging data. For instance, the path assessment component 104 can divide the medical imaging data into one or more data chunks based on volumetric features of the medical imaging data, surface features of the medical imaging data, location features of the medical imaging data, density features of the medical imaging data, geometric features of the medical imaging data and/or other features associated with the medical imaging data. However, it is to be appreciated that the path assessment component 104 can partition the medical imaging data into one or more data chunks based on a different technique. The path assessment component 104 can additionally or alternatively group data chunks associated with the medical imaging data based on content type and/or features associated with the medical imaging data.

For instance, the path assessment component 104 can group data chunks associated with the medical imaging data based on volumetric features of the medical imaging data, surface features of the medical imaging data, location features of the medical imaging data, density features of the medical imaging data, geometric features of the medical imaging data and/or other features associated with the medical imaging data. However, it is to be appreciated that the path assessment component 104 can group data chunks associated with the medical imaging data based on a different technique. Additionally or alternatively, the path assessment component 104 can divide the medical imaging data in to one or more data chunks and/or group data chunks associated with the medical imaging data based on a set of classifiers and/or object classes associated with the medical imaging data. In certain implementations, the path assessment component 104 can additionally or alternatively analyze the medical imaging data based on a statistical analysis technique. For example, the path assessment component 104 can analyze the medical imaging data based on a Markov random field technique.

The path recommendation component 106 can rank the implantation paths from the set of implantation paths. The path recommendation component 106 can also recommend a subset of the implantation paths for deployment of the medical device. In an aspect, the path recommendation component 106 can rank the implantation paths based on properties associated with the medical device and/or properties associated with the anatomic vessel. For instance, the path recommendation component 106 can rank the implantation paths based on mechanical properties associated with the medical device and/or mechanical properties associated with the anatomic vessel. Additionally or alternatively, the path recommendation component 106 can rank the implantation paths based on physical properties associated with the medical device and/or physical properties associated with the anatomic vessel. In an example, the path recommendation component 106 can compute and/or employ at least a rigid deformation value for the medical device and a rigid deformation value for the anatomic vessel to facilitate ranking of the implantation paths. Furthermore, the path recommendation component 106 can compute and/or employ a coefficient of restitution associated with the medical device and/or the anatomic vessel to facilitate ranking of the implantation paths. Therefore, the path recommendation component 106 can employ various properties for the medical device and/or the anatomic vessel to determine an implantation path along the anatomic vessel that is suitable for the medical device. Properties for the medical device can be determined based on a model representing the properties for the medical device. Furthermore, properties for the anatomic vessel can be determined based on a model representing properties for the anatomic vessel.

The path recommendation component 106 can additionally or alternatively rank the implantation paths based on a score that is determined for each of the implantation paths. A score can include a tortuosity score, an injury risk score, a intervention risk score and/or another type of score for the implantation path. For example, the path recommendation component 106 can calculate a score for each implantation path that is determined based on a number of turns associated with the anatomic vessel, a risk for causing damage to the anatomic vessel, a likelihood of performing another medical procedure in response to traversing the medical device through the anatomic vessel via a particular implantation path, etc. A score for an implantation path can also be determined based on a previous score computed for the implantation path. By employing the scores and various properties for the medical device and/or the anatomic vessel, the path recommendation component 106 can ensure that the medical device can properly traverse through the anatomical vessel while minimizing damage and/or risk to the anatomic vessel. For example, the path recommendation component 106 can determine whether the medical device is flexible enough to fit vessel curvature associated with the anatomic vessel, the path recommendation component 106 can ensure that the anatomic vessel is large enough to allow introduction and/or passage of the medical device, etc. The path recommendation component 106 can also employ a virtual simulation associated with the medical imaging data and the set of implantation paths. For example, the path recommendation component 106 can perform a virtual simulation implantation along each implantation path from the set of implantation paths to facilitate the ranking of the set of implantation paths.

In an example, the path recommendation component 106 can begin analysis of a particular implantation path from the set of implantation paths by virtually moving the medical device to a first portion of the anatomic vessel associated with the particular implantation path. At the first portion of the anatomic vessel, the path recommendation component 106 can compute a rigid deformation value for the medical device and another rigid deformation value for the first portion of the anatomic vessel. Then, the path recommendation component 106 can compute a coefficient of restitution associated with the medical device and the first portion of the anatomic vessel. The path recommendation component 106 can then generate a score for the particular implantation path based on the rigid deformation value for the medical device, the other rigid deformation value for the first portion of the anatomic vessel, and the coefficient of restitution. If the score satisfies a defined threshold value, the path recommendation component 106 can stop analysis of the particular implantation path. If the score does not satisfy a defined threshold value, the path recommendation component 106 can virtually move the medical device to a second portion of the anatomic vessel associated with the particular implantation path.

The path recommendation component 106 can analyze the second portion of the anatomic vessel by computing a new rigid deformation value for the medical device and another new rigid deformation value for the first portion of the anatomic vessel. A new coefficient of restitution associated with the medical device and the first portion of the anatomic vessel can also be computed by the path recommendation component 106. Then, the path recommendation component 106 update the score for the particular implantation path based on the new rigid deformation value for the medical device, the other new rigid deformation value for the first portion of the anatomic vessel, and the new coefficient of restitution. If the updated score satisfies a defined threshold value, the path recommendation component 106 can stop analysis of the particular implantation path. If the updated score does not satisfy a defined threshold value, the path recommendation component 106 can virtually move the medical device to a third portion of the anatomic vessel associated with the particular implantation path. The path recommendation component 106 can repeat this analysis process associated with the particular implantation path until the medical device reaches the lesion area. Additionally, the path recommendation component 106 can determine a device coverage factor regarding the lesion area during analysis of an implantation path. For example, if a device coverage factor falls below a defined threshold value during analysis of an implantation path, analysis of the implantation path can be discontinued.

The visualization component 108 can generate a display of the recommendations and a multi-dimensional visualization of the recommended subset of implantation paths for the deployment of the medical device. For example, the visualization component 108 can render a 3D visualization of the recommended subset of implantation paths on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. The multi-dimensional visualization of the recommended subset of implantation paths can be an interactive multi-dimensional visual sequence associated with an implantation path from the recommended subset of implantation paths. For example, the multi-dimensional visualization can present a multi-dimensional sequence of frames that depict different portions of the implantation path with respect to the medical device and the anatomic vessel. A first frame of the multi-dimensional sequence can depict a first portion of the implantation path associated with a first portion of the anatomic vessel and the medical device, a second frame of the multi-dimensional sequence can depict a second portion of the implantation path associated with a second portion of the anatomic vessel and the medical device, etc.

The anatomic vessel associated with the multi-dimensional sequence can be presented as a 3D rendering of the anatomic vessel. The medical device associated with the 3D visual sequence can also be presented as a 3D rendering of the medical device. A user can zoom into the frame of the multi-dimensional sequence, change a view associated with the frame of the multi-dimensional sequence, rotate a view associated with the 3D rendering of the anatomic vessel and/or the medical device, alter visual characteristics (e.g., color, shading, transparency, etc.) associated with the 3D rendering of the anatomic vessel and/or the medical device, etc. As such, a user can view, analyze and/or interact with a 3D rendering of the medical device as the medical device traverses through a 3D rendering of the anatomic vessel to the lesion area via an implantation path determined and/or assessed by the path recommendation component 106.

It is to be appreciated that technical features of the path analysis component 102 are highly technical in nature and not abstract ideas. Processing threads of the path analysis component 102 that process and/or analyze the medical imaging data, determine and/or access implantation paths, rank implantation paths, generated multi-dimensional visualizations associated with implantation paths, etc. cannot be performed by a human (e.g., are greater than the capability of a single human mind). For example, the amount of the medical imaging data processed, the speed of processing of the medical imaging data and/or the data types of the medical imaging data processed by the path analysis component 102 over a certain period of time can be respectively greater, faster and different than the amount, speed and data type that can be processed by a single human mind over the same period of time. Furthermore, the medical imaging data processed by the path analysis component 102 can be multi-dimensional data (e.g., 3D data) generated by sensors of a medical imaging device. Moreover, the path analysis component 102 can be fully operational towards performing one or more other functions (e.g., fully powered on, fully executed, etc.) while also processing the medical imaging data.

Figure 2:
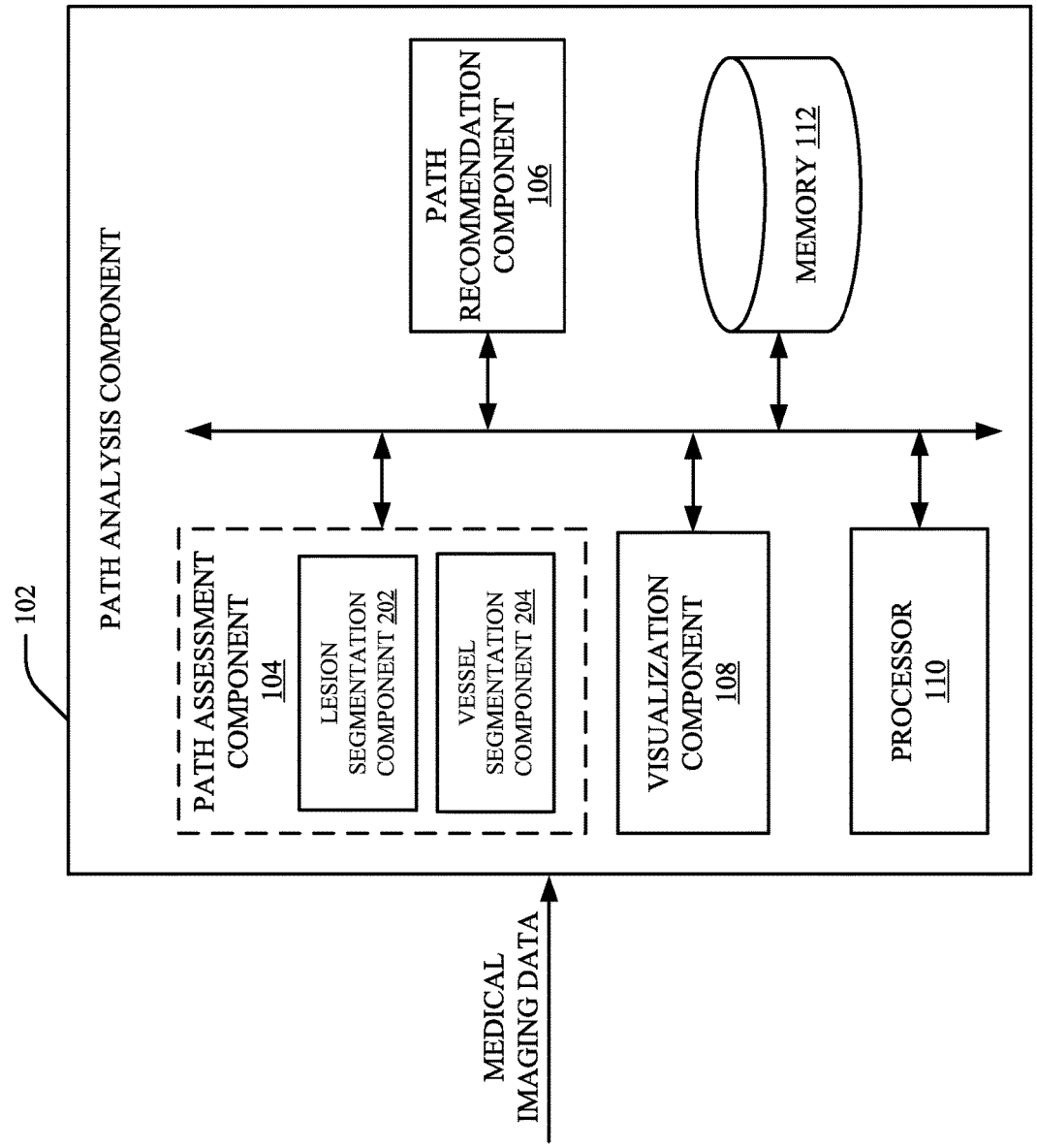

Referring now to FIG. 2, there is illustrated a non-limiting implementation of a system 200 in accordance with various aspects and implementations of this disclosure. The system 200 can include the path analysis component 102, and the path analysis component 102 can include the path assessment component 104, the path recommendation component 106 and the visualization component 108. The path assessment component 104 can include a lesion segmentation component 202 and a vessel segmentation component 204.

The lesion segmentation component 202 and the vessel segmentation component 204 can be employed to facilitate determination and/or assessment of implantation paths through an anatomic vessel (e.g., an implantation path for a medical device to reach a lesion area of an anatomic vessel). The lesion segmentation component 202 can perform segmentation with respect to the lesion area. For example, the lesion segmentation component 202 can identify and/or process a portion of the medical imaging data associated with the lesion area. The lesion segmentation component 202 can employ one or more segmentation algorithms and/or one or more statistical algorithms to perform segmentation with respect to a portion of the medical imaging data associated with the lesion area. The portion of the medical imaging data associated with the lesion area can be associated with geometric data for the lesion area, texture data associated with the lesion area and/or mesh data associated with the lesion area. The lesion segmentation component 202 can employ volumetric features, surface features, density features, geometric features, polygons, vectors, vertices, edges, faces and/or other features for the portion of the medical imaging data associated with the lesion area to facilitate segmentation of the lesion area.

The lesion segmentation component 202 can identify and/or process a portion of the medical imaging data associated with the lesion area based on a 3D edge detection technique. For example, the lesion segmentation component 202 can detect edge data from the medical imaging data indicative of edges related to the lesion area. The lesion segmentation component 202 can also identify and/or process a portion of the medical imaging data associated with the lesion area based on a classification technique. For example, the lesion segmentation component 202 can employ pattern recognition to classify a portion of the medical imaging data associated with the lesion area. Additionally or alternatively, the lesion segmentation component 202 can identify and/or process a portion of the medical imaging data associated with the lesion area based on a clustering technique. For example, the lesion segmentation component 202 can group portions of the medical imaging data based on similarities and/or matching criterion to facilitate identification and/or processing of a portion of the medical imaging data associated with the lesion area.

The vessel segmentation component 204 can perform segmentation with respect to the anatomic vessel. For example, the vessel segmentation component 204 can identify and/or process a portion of the medical imaging data associated with the anatomic vessel. The vessel segmentation component 204 can employ one or more segmentation algorithms and/or one or more statistical algorithms to perform segmentation with respect to a portion of the medical imaging data associated with the anatomic vessel. The portion of the medical imaging data associated with the anatomic vessel can be associated with geometric data for the anatomic vessel, texture data associated with the anatomic vessel and/or mesh data associated with the anatomic vessel. The vessel segmentation component 204 can employ volumetric features, surface features, density features, geometric features, polygons, vectors, vertices, edges, faces and/or other features for the portion of the medical imaging data associated with the anatomic vessel to facilitate segmentation of the anatomic vessel.

The vessel segmentation component 204 can identify and/or process a portion of the medical imaging data associated with the anatomic vessel based on a 3D edge detection technique. For example, the vessel segmentation component 204 can detect edge data from the medical imaging data indicative of edges related to the anatomic vessel. The vessel segmentation component 204 can also identify and/or process a portion of the medical imaging data associated with the anatomic vessel based on a classification technique. For example, the vessel segmentation component 204 can employ pattern recognition to classify a portion of the medical imaging data associated with the anatomic vessel. Additionally or alternatively, the vessel segmentation component 204 can identify and/or process a portion of the medical imaging data associated with the anatomic vessel based on a clustering technique. For example, the vessel segmentation component 204 can group portions of the medical imaging data based on similarities and/or matching criterion to facilitate identification and/or processing of a portion of the medical imaging data associated with the anatomic vessel.

Figure 3:
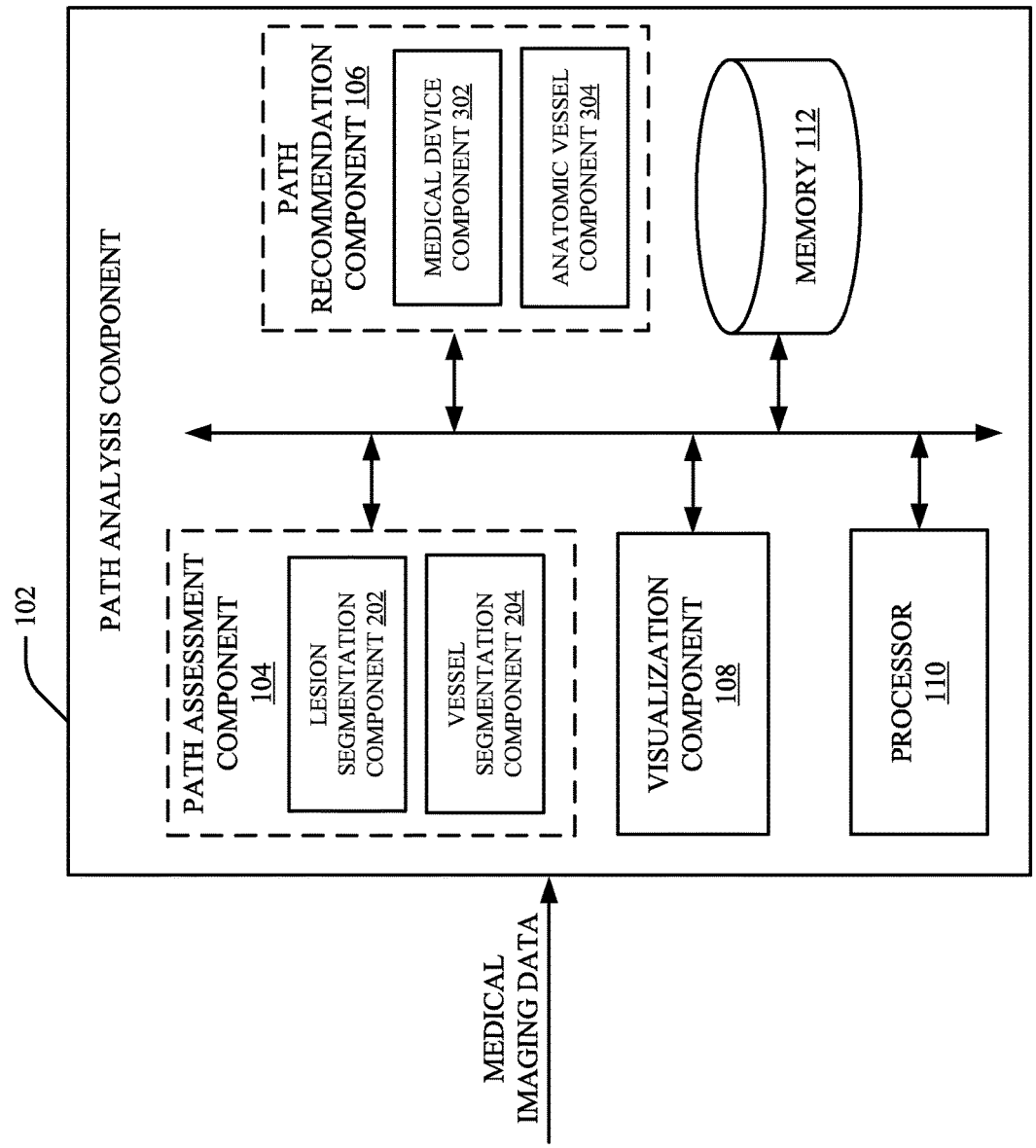

Referring to FIG. 3, there is illustrated a non-limiting implementation of a system 300 in accordance with various aspects and implementations of this disclosure. The system 300 can include the path analysis component 102, and the path analysis component 102 can include the path assessment component 104, the path recommendation component 106 and the visualization component 108. The path assessment component 104 can include a lesion segmentation component 202 and a vessel segmentation component 204. Additionally, the path recommendation component 106 can include a medical device component 302 and an anatomic vessel component 304.

The medical device component 302 can determine and/or provide properties associated with the medical device to facilitate analysis and/or ranking of the set of implantation paths. For example, medical device component 302 can determine and/or provide mechanical properties and/or physical properties of the medical device. Mechanical properties and/or physical properties associated with the medical device can include, for example, flexibility of the medical device, rigidity of the medical device, a coefficient of restitution of the medical device, deformation potential of the medical device, strength of the medical device, surface tension of the medical device, elasticity of the medical device, a coefficient of friction of the medical device, compressive strength of the medical device, ductility of the medical device, malleability of the medical device, resilience of the medical device, surface roughness of the medical device, stiffness of the medical device, toughness of the medical device, hardness of the medical device, a size of the medical device, a shape of the medical device, a length of the medical device, a circumference of the medical device, a thickness of the medical device, elasticity of the medical device, material of the medical device and/or another property of the medical device. In an aspect, the medical device component 302 can determine properties associated with the medical device based on a model associated with the medical device. In another aspect, the medical device component 302 can store and/or access a list of medical devices and associated properties to determine properties associated with the medical device. For example, properties of the medical device can be previously determined using one or more measuring tools and/or one or more quantitative metric techniques.

The anatomic vessel component 304 can determine and/or provide properties associated with the anatomic vessel to facilitate analysis and/or ranking of the set of implantation paths. For example, anatomic vessel component 304 can determine and/or provide mechanical properties and/or physical properties of the anatomic vessel. Mechanical properties and/or physical properties associated with the anatomic vessel can include, for example, flexibility of anatomic vessel, rigidity of the anatomic vessel, a coefficient of restitution of the anatomic vessel, deformation potential of the anatomic vessel, strength of the anatomic vessel, surface tension of the anatomic vessel, elasticity of the anatomic vessel, a coefficient of friction of the anatomic vessel, strength of the anatomic vessel, resilience of the anatomic vessel, surface roughness of the anatomic vessel, stiffness of the anatomic vessel, toughness of the anatomic vessel, hardness of the anatomic vessel, a size of the anatomic vessel, a shape of the anatomic vessel, a length of the anatomic vessel, a circumference of the anatomic vessel, a thickness of the anatomic vessel, elasticity of the anatomic vessel, an anatomic substance of the anatomic vessel and/or another property of the anatomic vessel. In an aspect, the anatomic vessel component 304 can determine properties associated with the anatomic vessel based on a model associated with the anatomic vessel. In another aspect, the anatomic vessel component 304 can store and/or access other medical imaging data and/or other medical records to determine properties associated with the anatomic vessel.

Figure 4:
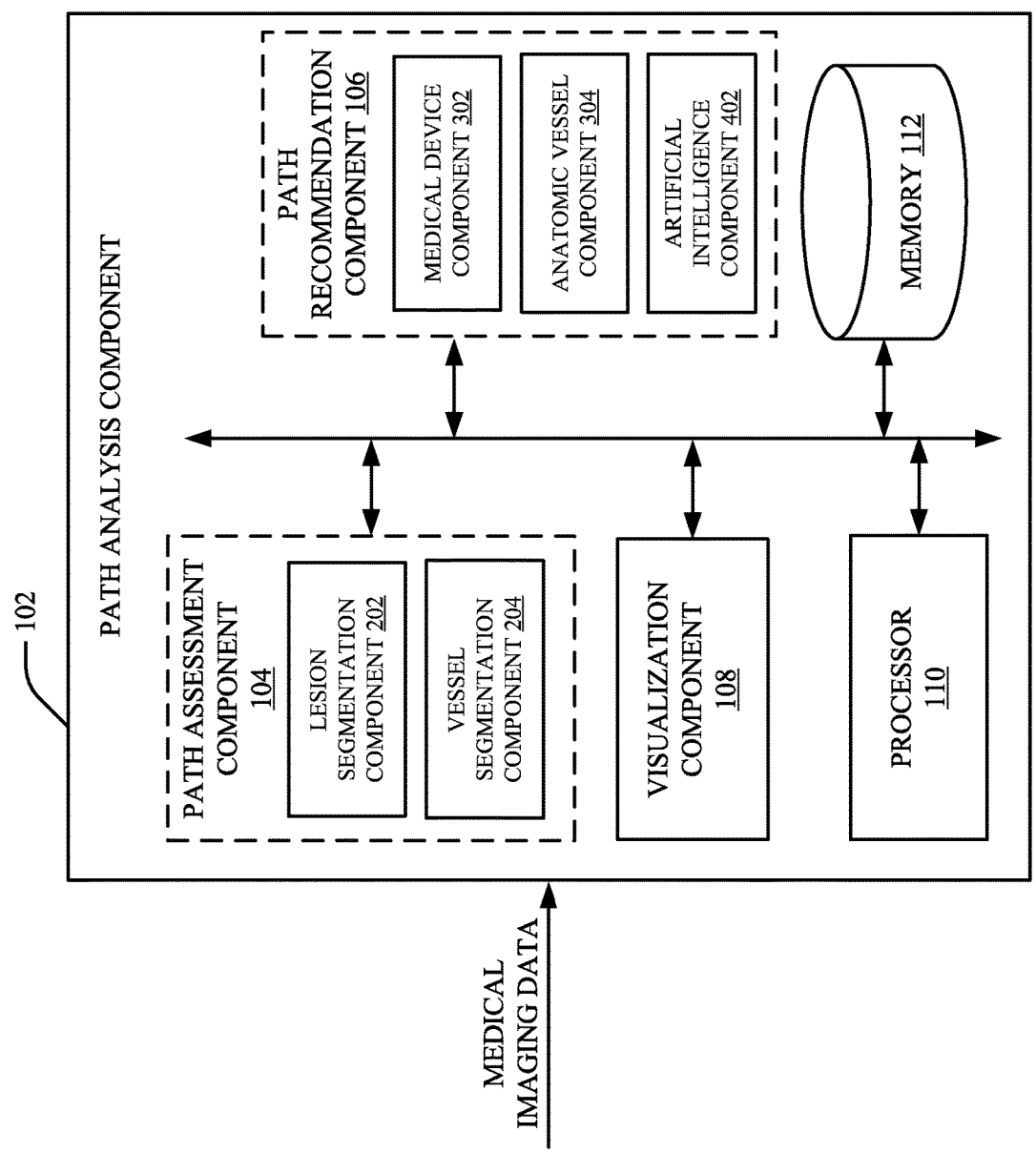

Referring to FIG. 4, there is illustrated a non-limiting implementation of a system 400 in accordance with various aspects and implementations of this disclosure. The system 400 can include the path analysis component 102, and the path analysis component 102 can include the path assessment component 104, the path recommendation component 106 and the visualization component 108. The path assessment component 104 can include a lesion segmentation component 202 and a vessel segmentation component 204. Additionally, the path recommendation component 106 can include the medical device component 302, the anatomic vessel component 304 and an artificial intelligence component 402.

The artificial intelligence component 402 can perform a probabilistic based utility analysis that weighs costs and benefits associated with each of the implantation paths to reach the lesion area. To facilitate analysis and/or ranking of the set of implantation paths, the artificial intelligence component 402 can employ principles of artificial intelligence to facilitate learning and/or generating inferences for the set of implantation paths. The artificial intelligence component 402 can perform learning with respect to the set of implantation paths explicitly or implicitly. The learning and/or generated inferences by the artificial intelligence component 402 can facilitate identification and/or classification of different characteristics associated with respective implantation paths from the set of implantation paths.

The artificial intelligence component 402 can also employ an automatic classification system and/or an automatic classification process to facilitate learning and/or generating inferences for set of implantation paths. For example, the artificial intelligence component 402 can employ a probabilistic and/or statistical-based analysis (e.g., factoring into the analysis utilities and costs) to learn and/or generate inferences for the set of implantation paths. The artificial intelligence component 402 can employ, for example, a support vector machine (SVM) classifier to learn and/or generate inferences for the set of implantation paths. Additionally or alternatively, the artificial intelligence component 402 can employ other classification techniques associated with Bayesian networks, decision trees and/or probabilistic classification models. Classifiers employed by the artificial intelligence component 402 can be explicitly trained (e.g., via a generic training data) as well as implicitly trained (e.g., via receiving extrinsic information). For example, with respect to SVM's that are well understood, SVM's are configured via a learning or training phase within a classifier constructor and feature selection module. A classifier is a function that maps an input attribute vector, $x=(x1, x2, x3, x4, xn)$, to a confidence that the input belongs to a class— that is, $f(x)=confidence(class)$.

In an aspect, the artificial intelligence component 402 can include an inference component that can further enhance automated aspects of the artificial intelligence component 402 utilizing in part inference based schemes to facilitate learning and/or generating inferences for the set of implantation paths. The artificial intelligence component 402 can employ any suitable machine-learning based techniques, statistical-based techniques and/or probabilistic-based techniques. For example, the artificial intelligence component 402 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the artificial intelligence component 402 can perform a set of machine learning computations associated with the set of implantation paths. For example, the artificial intelligence component 402 can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations.

Figure 5:
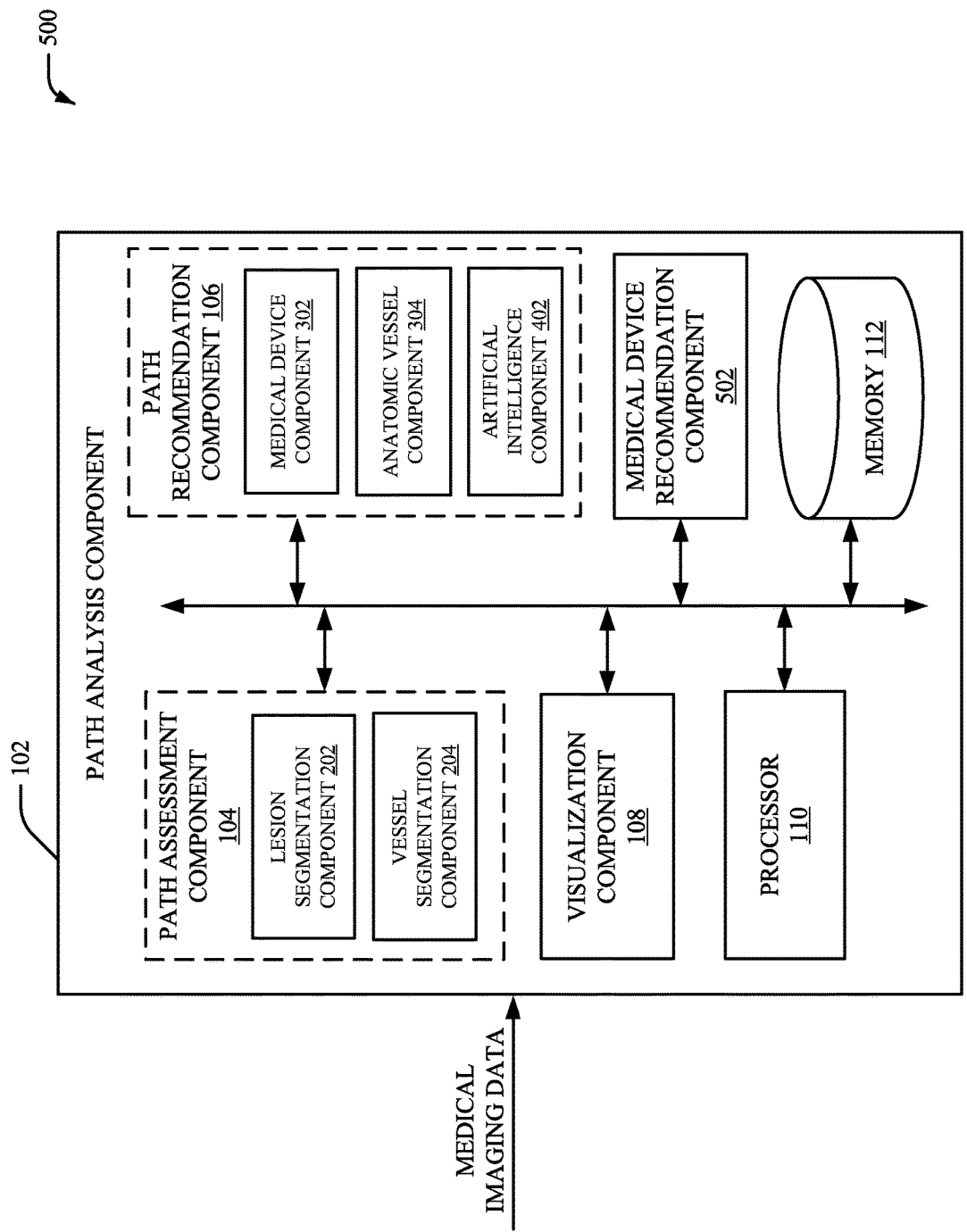

Referring to FIG. 5, there is illustrated a non-limiting implementation of a system 500 in accordance with various aspects and implementations of this disclosure. The system 500 can include the path analysis component 102, and the path analysis component 102 can include the path assessment component 104, the path recommendation component 106, the visualization component 108 and/or a medical device recommendation component 502. The path assessment component 104 can include a lesion segmentation component 202 and a vessel segmentation component 204. Additionally, the path recommendation component 106 can include the medical device component 302, the anatomic vessel component 304 and an artificial intelligence component 402.

The medical device recommendation component 502 can recommend and/or select a medical device to be implanted and traversed along an implantation path associated with an anatomic vessel. For example, the medical device recommendation component 502 can recommend, based on the path assessment component analyses, a subset of available medical devices to be deployed into an anatomic vessel via an implantation path recommended by the path recommendation component 106. The medical device recommendation component 502 can recommend and/or select a medical device based on properties associated with the anatomic vessel and/or properties associated with the medical device. For example, the medical device recommendation component 502 can select a medical device based in part on flexibility of the medical device to fit vessel curvature of the anatomic vessel. Additionally or alternatively, the medical device recommendation component 502 can select a medical device based in part on a size of the medical device to fit a cross-sectional area of the anatomic vessel. The medical device recommendation component 502 can recommend and/or select a medical device after an implantation path is determined for an anatomic vessel. Alternatively, the medical device recommendation component 502 can recommend and/or select a medical device during analysis of an implantation path to facilitate selection and/or recommendation of an implantation path by the path recommendation component 106.

Recommendation and/or selection of a medical device by the medical device recommendation component 502 can also be determined based on a lesion area of an anatomic vessel and/or user input data. For example, the medical device recommendation component 502 can recommend and/or select a medical device for an implantation path based on a type of medical procedure being performed and/or preferences of a medical professional performing the medical procedure. In an aspect, the medical device recommendation component 502 can rank medical devices in a subset of available medical devices (e.g., a subset of available medical devices to be deployed into an anatomic vessel via an implantation path). For example, the medical device recommendation component 502 can rank available medical devices based on correlations between medical devices and an implantation path, risks associated with employing a medical device for an implantation path, difficulty for using a medical device for an implantation path, etc. In certain implementations, the medical device recommendation component 502 can employ information provided by the artificial intelligence component 402 to facilitate selection an/or ranking of available medical devices for an implantation path.

Figure 6:
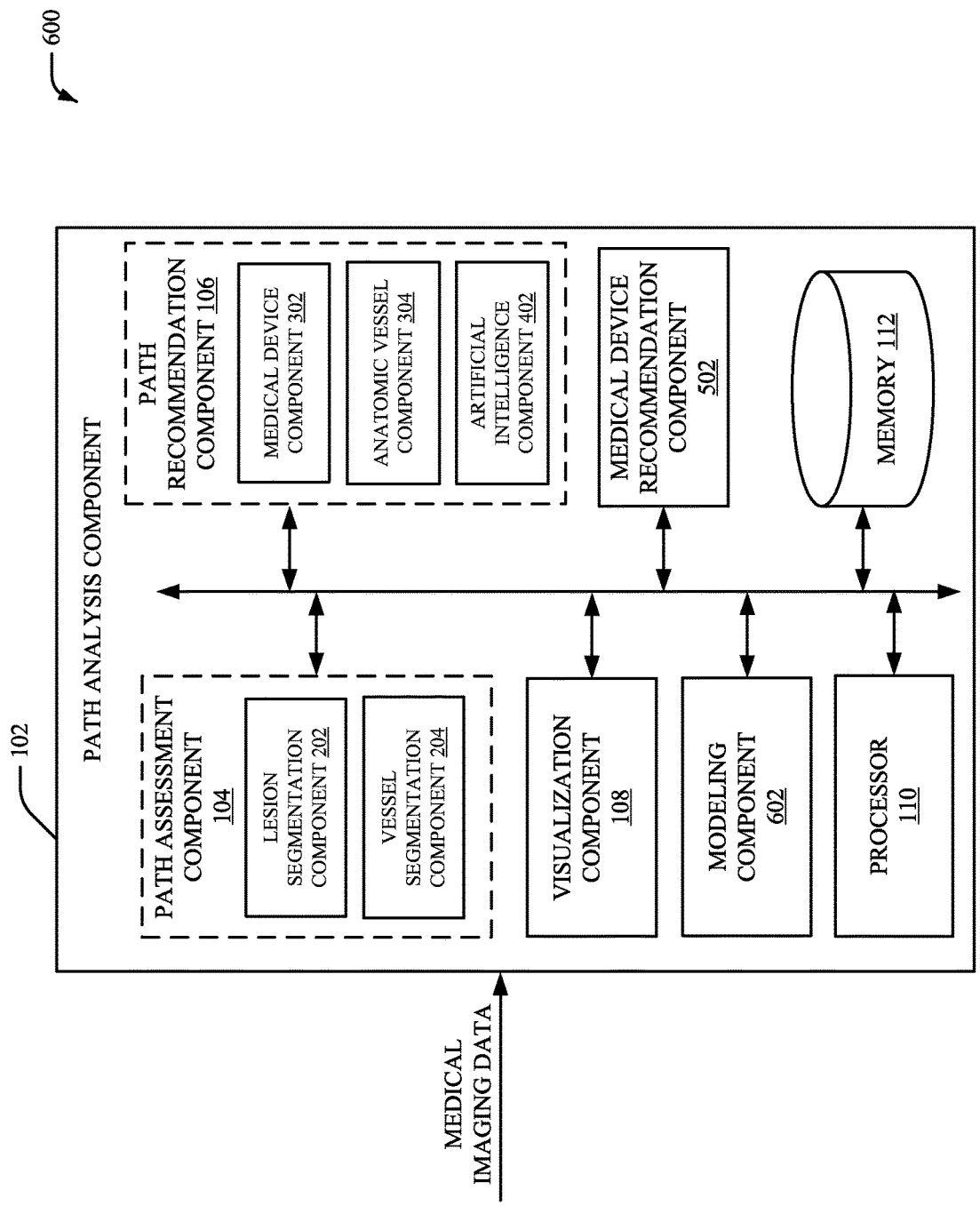

Referring to FIG. 6, there is illustrated a non-limiting implementation of a system 600 in accordance with various aspects and implementations of this disclosure. The system 600 can include the path analysis component 102, and the path analysis component 102 can include the path assessment component 104, the path recommendation component 106, the visualization component 108, the medical device recommendation component 502 and/or a modeling component 602. The path assessment component 104 can include a lesion segmentation component 202 and a vessel segmentation component 204. Additionally, the path recommendation component 106 can include the medical device component 302, the anatomic vessel component 304 and an artificial intelligence component 402. The modeling component 602 can generate, based at least in part on analysis by the path assessment component 104 and/or the path recommendation component 106, a model for a suitable medical device to be deployed to a lesion area of an anatomic vessel via an implantation path. For example, the modeling component 602 can generate a 3D printing model of a medical device to be deployed to a lesion area of an anatomic vessel via an implantation path. The modeling component 602 can generate a computer aided design (CAD) model of a medical device to be deployed to a lesion area of an anatomic vessel via an implantation path. Furthermore, the modeling component 602 can employ the medical imaging data to facilitate generation of the model for the medical device. Properties and/or characteristics of the model for the medical device can be determined based on properties and/or characteristics of an implantation path for the medical device, an anatomic vessel associated with the implantation path, and/or a lesion area associated with the implantation path. For example, the model generated by the modeling component 602 can be tailored to the implantation path recommended by the path recommendation component 106.

Figure 7:
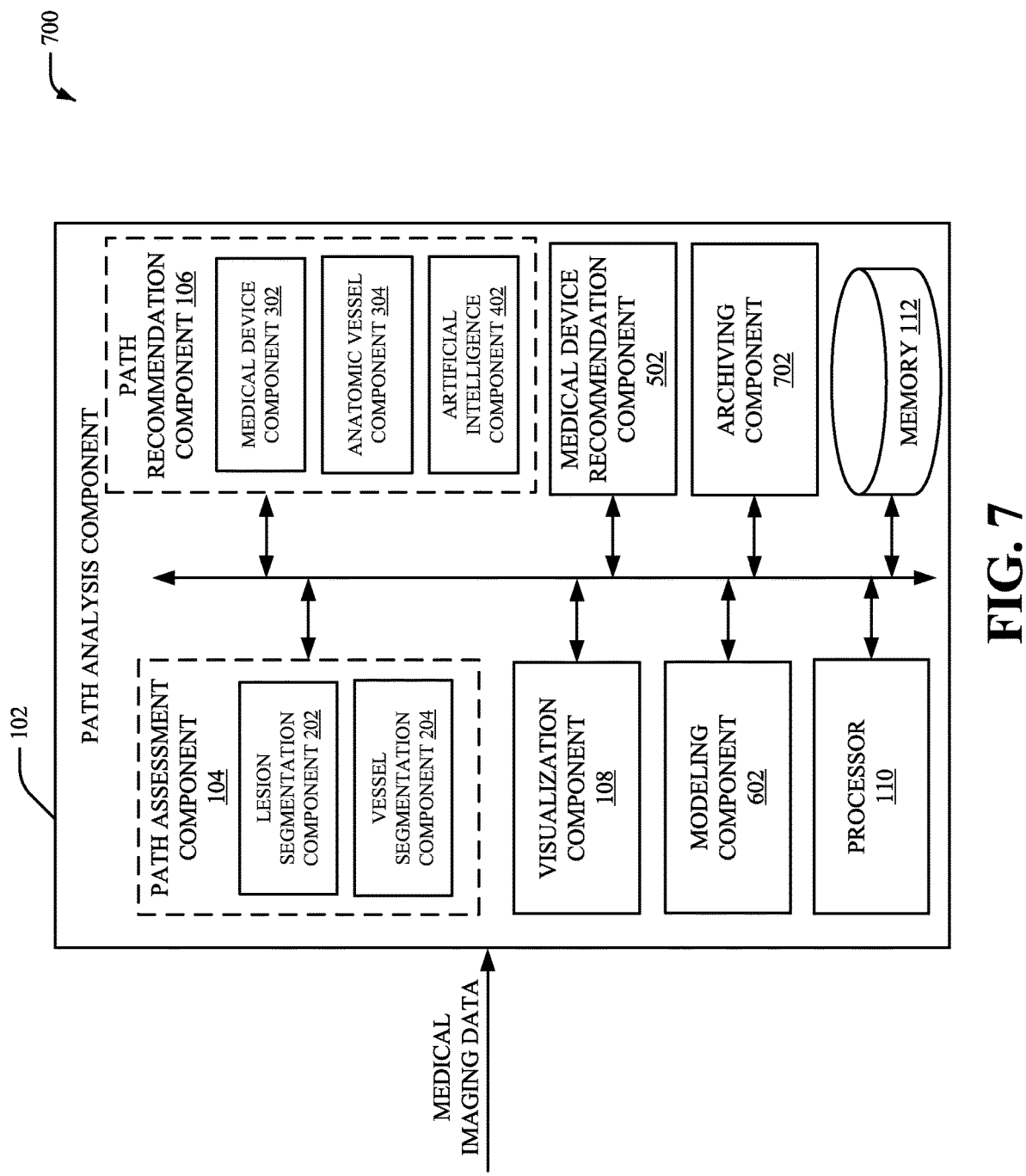

Referring to FIG. 7, there is illustrated a non-limiting implementation of a system 700 in accordance with various aspects and implementations of this disclosure. The system 700 can include the path analysis component 102, and the path analysis component 102 can include the path assessment component 104, the path recommendation component 106, the visualization component 108, the medical device recommendation component 502, the modeling component 602 and/or an archiving component 702. The path assessment component 104 can include a lesion segmentation component 202 and a vessel segmentation component 204. Additionally, the path recommendation component 106 can include the medical device component 302, the anatomic vessel component 304 and an artificial intelligence component 402.

The archiving component 702 can store data determined by the path recommendation component 106, the visualization component 108 and/or the medical device recommendation component 502 and/or the modeling component 602. For example, data regarding a implantation path assessments, recommended implantation path and/or a ranking determined by the path recommendation component 106 can be archived and/or stored by the archiving component 702. Additionally or alternatively, data for a multi-dimensional visualization associated with an implantation path, an anatomic vessel and/or a medical device can be archived and/or stored by the archiving component 702. Data regarding medical device that is recommended by the medical device recommendation component 502 can additionally or alternatively be archived and/or stored by the archiving component 702. Additionally or alternatively, data for a model generated by the modeling component 602 can be archived and/or stored by the archiving component 702. Information stored and/or archived by the archiving component 702 can facilitate presentation of rendered data to a user and/or recommendation of implantation paths and/or medical devices to a user. Information stored and/or archived by the archiving component 702 can also facilitate a medical procedure associated with the medical device and/or the anatomic vessel, clinician reporting, a 3D printing process associated with the medical device, etc.

Figure 8:
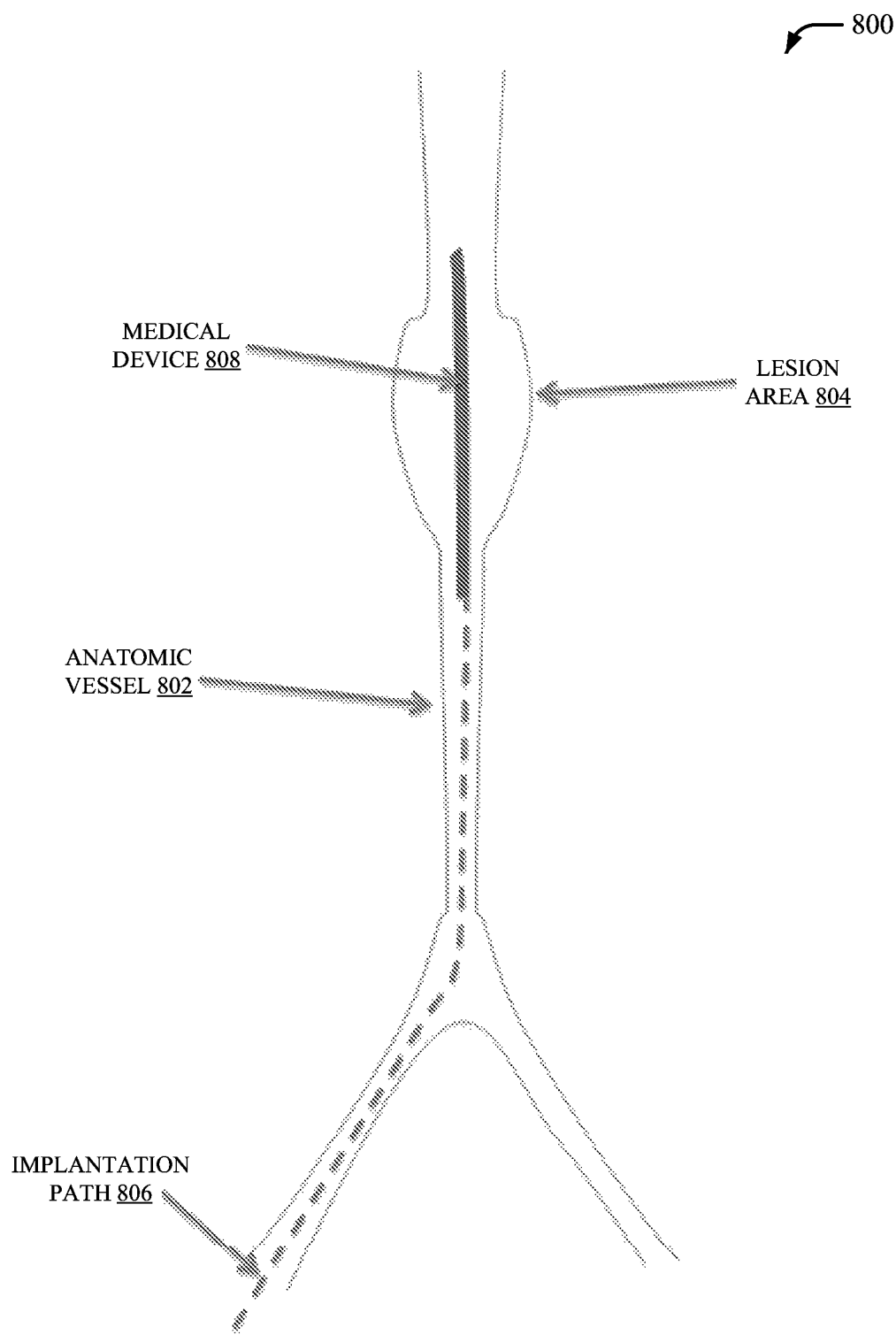
FIG. 8 illustrates an example anatomic vessel associated with an implantation path, in accordance with various aspects and implementations described herein.

Referring now to FIG. 8, there is illustrated a non-limiting implementation of a system 800 in accordance with various aspects and implementations of this disclosure. The system 800 includes an anatomic vessel 802 of a patient body. Medical imaging data associated with the anatomic vessel 802 can be generated by employing one or more medical imaging devices. The medical imaging data associated with the anatomic vessel 802 can be multi-dimensional medical imaging data (e.g., 3D medical imaging data). Furthermore, the path analysis component 102 can receive the medical imaging data associated with the anatomic vessel 802. The path assessment component 104 can analyze the medical imaging data associated with the anatomic vessel 802. For example, the path assessment component 104 can perform segmentation associated with the anatomic vessel 802. Furthermore, the path assessment component 104 can perform segmentation associated with a lesion area 804 of the anatomic vessel 802. The lesion area 804 can be, for example, a disease area of the anatomic vessel 802. The path analysis component 102 can determine an implantation path 806 for a medical device 808 to reach the lesion area 804. For example, the path assessment component 104 can generate a set of candidate implantation paths for the medical device 808 to reach the lesion area 804. The medical device 808 can be, for example, a stent (e.g., a vascular stent). Then, the path recommendation component 106 can rank the set of candidate implantation paths based on at least properties associated with the anatomic vessel 802 and/or properties associated with the medical device 808. Based on the ranking of the set of candidate implantation paths, the path recommendation component 106 can recommend the implantation path 806 from the set of candidate implantation paths for deployment of the medical device 808 to the lesion area 804. The path recommendation component 106 ensures that the medical device 808 is flexible enough to fit vessel curvature of the anatomic vessel 802 and/or ensures that a diameter of the anatomic vessel 802 is large enough to allow introduction of the medical device 808.

Figure 9:
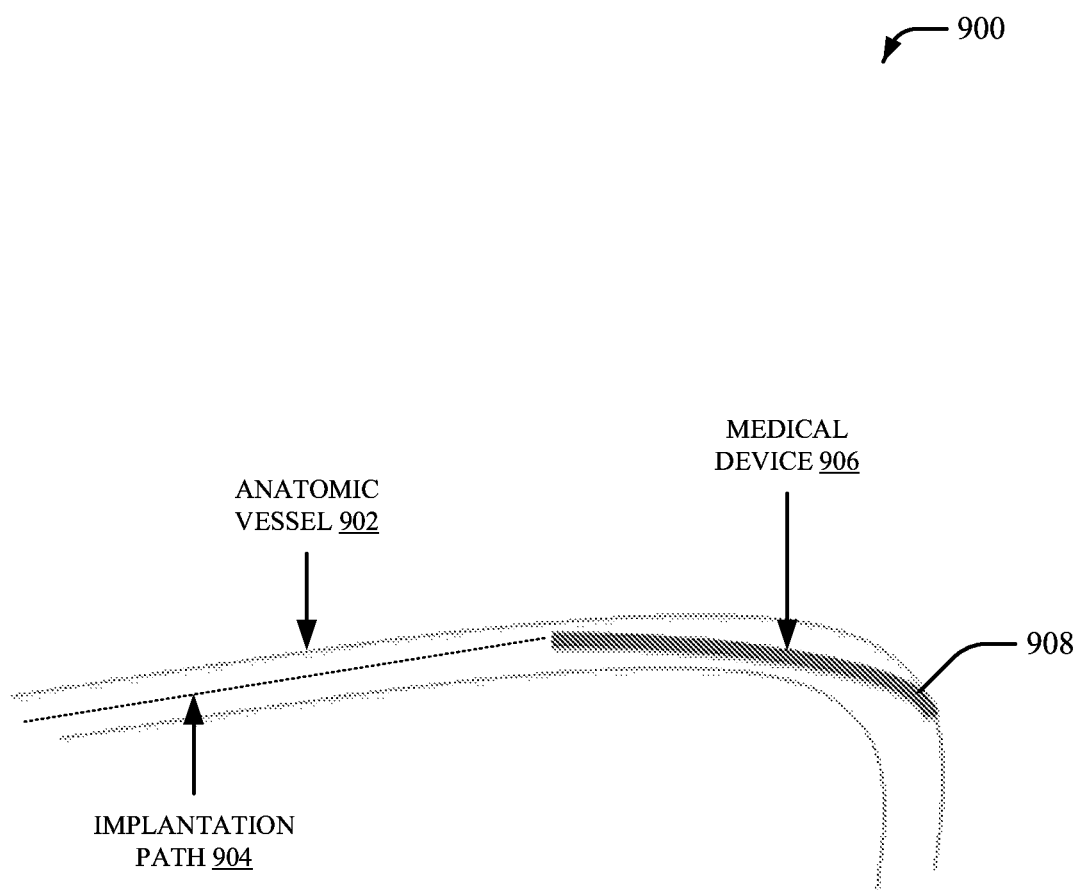
FIG. 9 illustrates another example anatomic vessel associated with an implantation path, in accordance with various aspects and implementations described herein.

Referring now to FIG. 9, there is illustrated a non-limiting implementation of a system 900 in accordance with various aspects and implementations of this disclosure. The system 900 includes an anatomic vessel 902 of a patient body. With a conventional implantation procedure, a medical professional interprets 2D medical data associated with the anatomic vessel to guess an implantation path 904 for a medical device 906. Then, through trial and error, a medical professional physically inserts the medical device 906 into the anatomic vessel 902. However, with the conventional implantation procedure, the medical device 906 would physically come into contact with a vessel wall of the anatomic vessel 902 at a location 908 associated with the anatomic vessel 902. In contrast, with the path analysis component 102, multi-dimensional medical imaging data (e.g., 3D medical imaging data) for the anatomic vessel 902 that is generated by one or more medical imaging devices can be employed. Then, based on analysis of the multi-dimensional medical imaging data associated with the anatomic vessel 902, the path analysis component 102 can determine that an implantation path 904 is not suitable for a medical device 906. For example, with the path analysis component 102, it can be determined that the medical device 906 comes into contact with a vessel wall of the anatomic vessel 902 at the location 908. The path analysis component 102 can determine that properties of the medical device 906 are not adequate to fit vessel curvature associated with the anatomic vessel 902. In response to a determination by the path analysis component 102 that the medical device 906 is not adequate for the implantation path 904, the path analysis component 102 can select a different implantation path and/or a different medical device for the implantation path 904. As such, a medical procedure for implanting the medical device 906 into the anatomic vessel 902 can be more efficient and/or more accurate. Furthermore, invasive procedures to the anatomic vessel 902 can be minimized by replacing human trial and error for implanting the medical device 906 in the anatomic vessel 902.

FIGS. 10-13 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Figure 10:
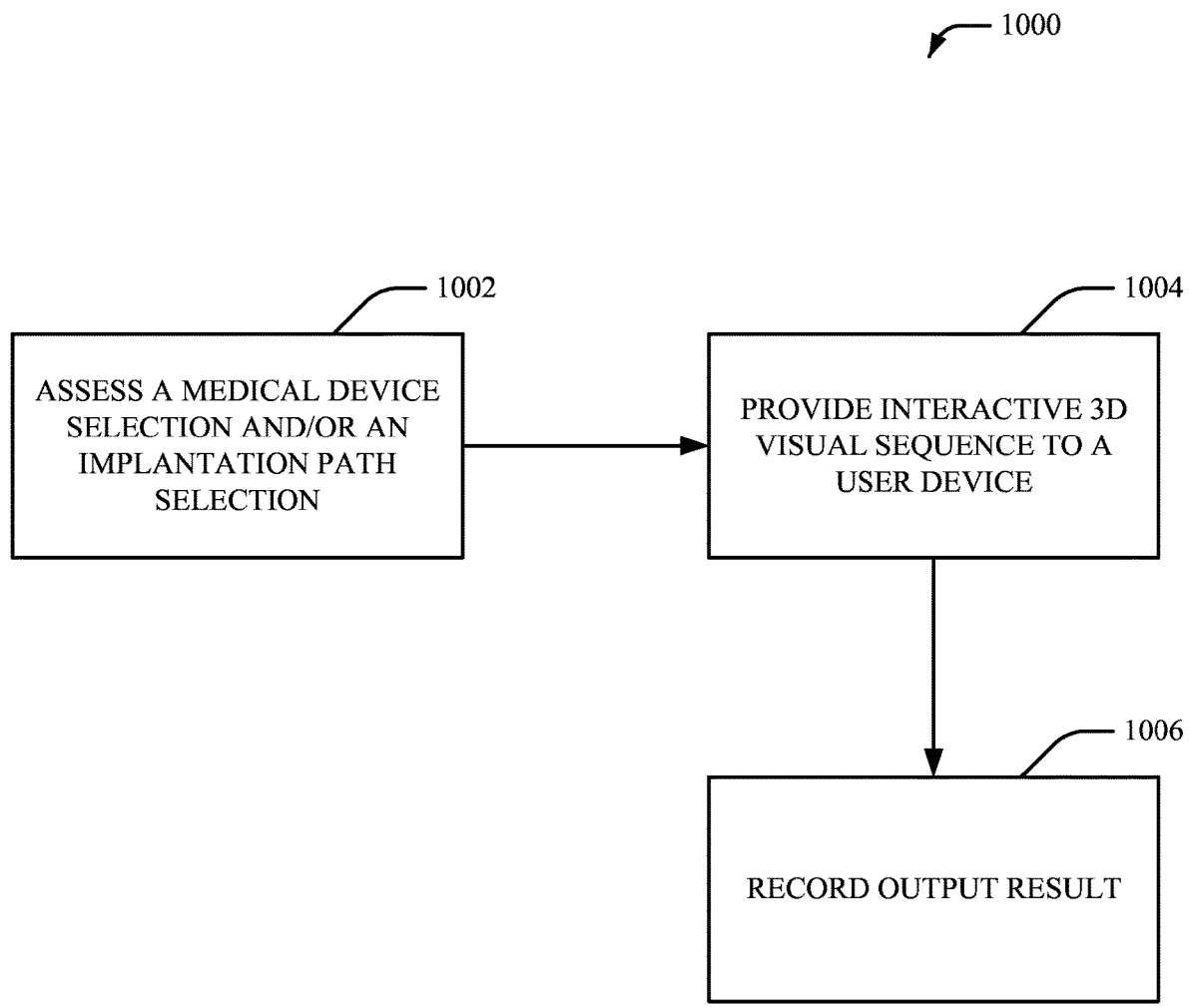
FIG. 10 depicts a flow diagram of an example method for assessing an implantation path for a medical device, in accordance with various aspects and implementations described herein.

Referring to FIG. 10, there is illustrated a non-limiting implementation of a methodology 1000 for assessing an implantation path for a medical device, according to an aspect of the subject innovation. At 1002, a medical device selection and/or an implantation path selection is assessed (e.g., by the path analysis component 102). For example, a medical device and/or an implantation path for the medical device can be selected by segmenting and/or analyzing medical imaging data. Mechanical properties and/or physical properties of the medical device and/or an anatomic vessel associated with the implantation path can be employed to select the medical device and/or the implantation path. Assessment of the medical device selection and/or the implantation path selection can include confirming that the medical device is suitable for employment via the implantation path. For example, it can be confirmed that the medical device is adequately flexible to fit curvature of the anatomic vessel associated with the implantation path, it can be confirmed that an opening of the anatomic vessel is large enough to allow the medical device to be inserted and traversed via the implantation path. Assessment of the medical device selection and/or the implantation path selection can also include virtually simulating an implantation process associated with the implantation path and the medical device.

At 1004, an interactive 3D visual sequence is provided to a user device. For example, a display of a user device can present an interactive 3D visual sequence to allow a user to view and/or analyze the selected medical device and/or the selected implantation path via the interactive 3D visual sequence. In an aspect, the 3D visual sequence can present a series of frames that depict different portions of the implantation path with respect to the medical device and the anatomic vessel. For example, a first frame of the 3D visual sequence can depict a first portion of the implantation path associated with a first portion of the anatomic vessel and the medical device, a second frame of the 3D visual sequence can depict a second portion of the implantation path associated with a second portion of the anatomic vessel and the medical device, etc. The anatomic vessel associated with the 3D visual sequence can be presented as a 3D rendering of the anatomic vessel and/or the medical device associated with the 3D visual sequence can be presented as a 3D rendering of the medical device.

At 1006, an output result is recorded. For example, information regarding an implantation path that is a most advantageous implantation path to reach a lesion area of the anatomic vessel with the medical device can be archived and/or stored. In one example, the information regarding the implantation path can be stored to facilitate use of the information regarding the implantation path prior to or during a medical procedure associated with the medical device and the anatomic vessel. In another example, the information regarding the implantation path can be stored to facilitate clinician reporting. In yet another example, the information regarding the implantation path can be stored to facilitate a 3D printing process associated with the medical device and/or the anatomic vessel.

Figure 11:
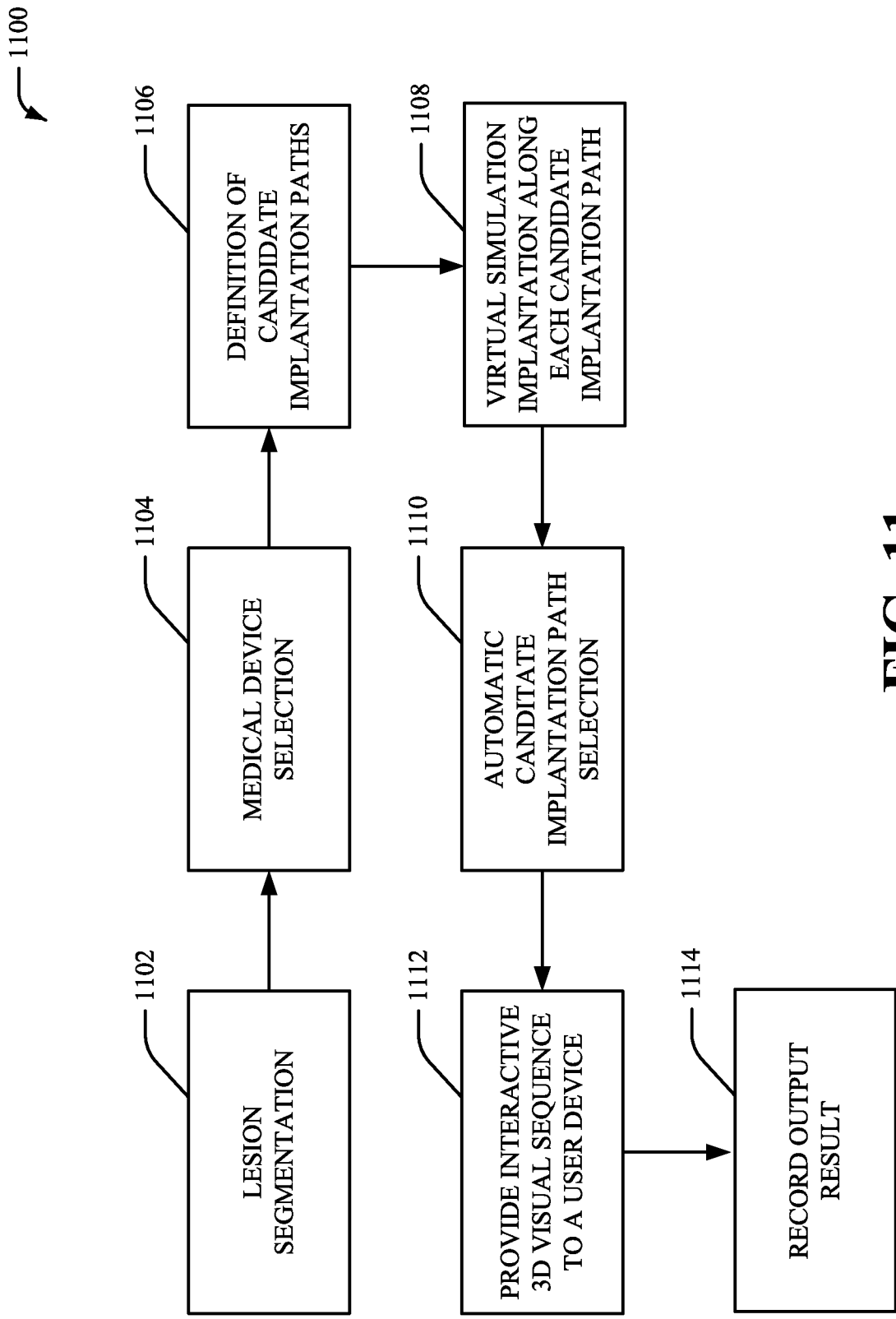
FIG. 11 depicts a flow diagram of an example method for determining an implantation path for a medical device, in accordance with various aspects and implementations described herein.

Referring now to FIG. 11, there is illustrated a non-limiting implementation of a methodology 1100 for determining an implantation path for a medical device, according to an aspect of the subject innovation. At 1102, lesion segmentation is performed. For example, segmentation is performed for a portion of medical imaging data associated with a lesion area of an anatomic vessel. The lesion segmentation can define the lesion area from the medical imaging data. At 1104, a medical device is selected. For example, a medical device can be chosen and a model representing mechanical properties of the medical device can be generated. At 1106, candidate implantation paths are defined. For example, all possible implantation paths for the medical device to reach the lesion can be defined. A model representing mechanical properties of the anatomic vessel can also be generated. Moreover, a model of the anatomic vessel can be generated. At 1108, virtual simulation implantation is performed along each candidate implantation path. For example, the medical device can be virtually traversed through each candidate implantation path associated with the anatomic vessel. At 1110, a candidate implantation path is automatically selected. For example, a most advantageous implantation path for the medical device to reach the lesion area associated with the anatomic vessel can be determined.

At 1112, an interactive 3D visual sequence is provided to a user device. For example, a display of a user device can present an interactive 3D visual sequence to allow a user to view and/or analyze the selected medical device and/or the selected implantation path via the interactive 3D visual sequence. In an aspect, the 3D visual sequence can present a series of frames that depict different portions of the implantation path with respect to the medical device and the anatomic vessel. For example, a first frame of the 3D visual sequence can depict a first portion of the implantation path associated with a first portion of the anatomic vessel and the medical device, a second frame of the 3D visual sequence can depict a second portion of the implantation path associated with a second portion of the anatomic vessel and the medical device, etc. The anatomic vessel associated with the 3D visual sequence can be presented as a 3D rendering of the anatomic vessel and/or the medical device associated with the 3D visual sequence can be presented as a 3D rendering of the medical device. At 1114, an output result is recorded. For example, information regarding an implantation path that is a most advantageous implantation path to reach a lesion area of the anatomic vessel with the medical device can be archived and/or stored. In one example, the information regarding the implantation path can be stored to facilitate use of the information regarding the implantation path prior to or during a medical procedure associated with the medical device and the anatomic vessel. In another example, the information regarding the implantation path can be stored to facilitate clinician reporting. In yet another example, the information regarding the implantation path can be stored to facilitate a 3D printing process associated with the medical device and/or the anatomic vessel.

Figure 12:
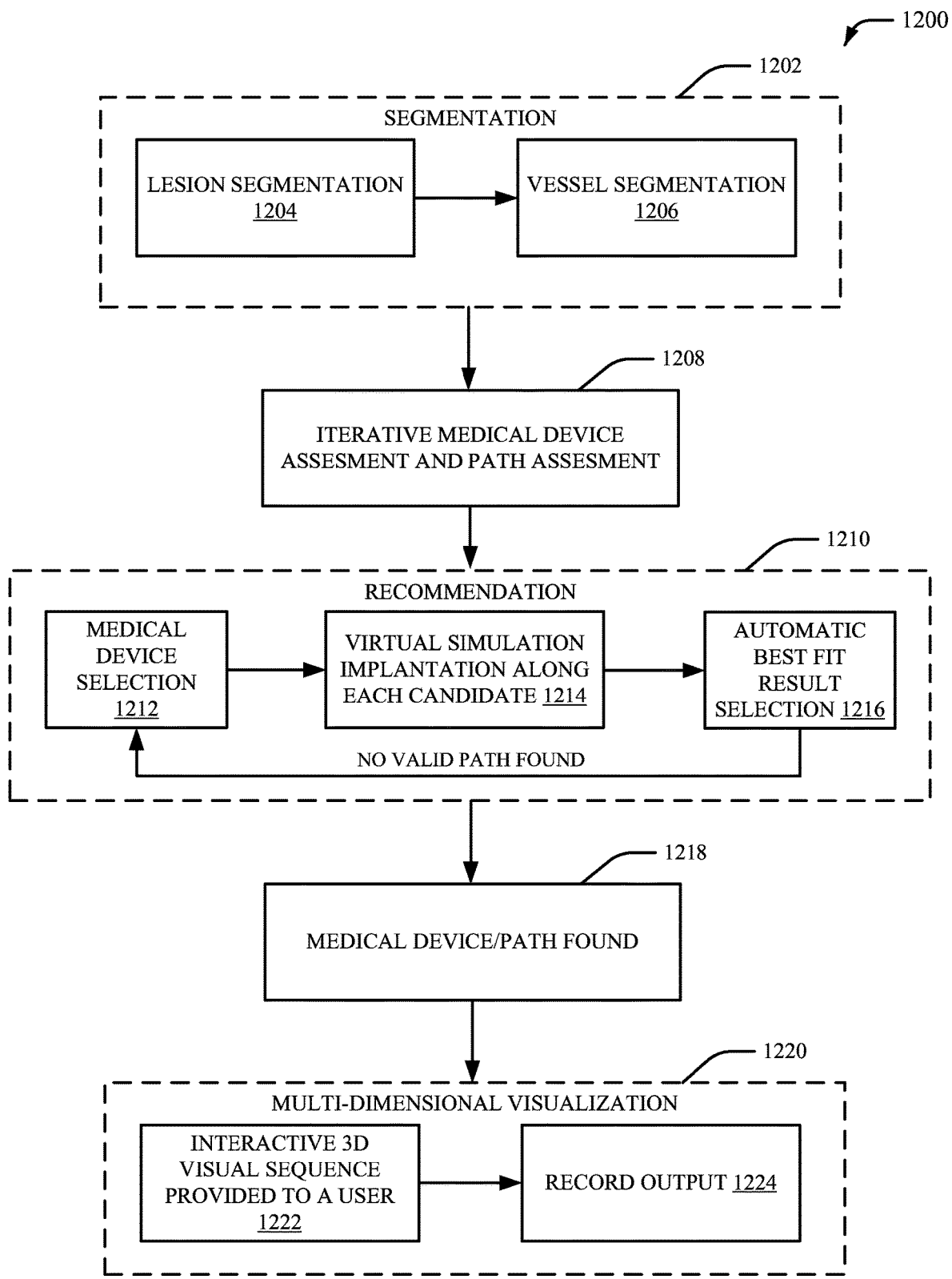
FIG. 12 depicts a flow diagram of an example method for segmenting, recommending and displaying an implantation path for a medical device, in accordance with various aspects and implementations described herein.

Referring now to FIG. 12, there is illustrated a non-limiting implementation of a methodology 1200 for segmenting, recommending and displaying an implantation path for a medical device, according to an aspect of the subject innovation. At 1202, segmentation is performed with respect to medical imaging data (e.g., multi-dimensional medical imaging data). Segmentation can include a step 1204 where lesion segmentation is performed. For example, a lesion area associated with an anatomic vessel can be defined from the medical imaging data. Segmentation can also include a step 1206 where vessel segmentation is performed. For instance, the anatomic vessel can also be defined from the medical imaging data. At 1208, iterative medical device assessment and path assessment is performed. For example, instead of validating a medical device into different implantation path, the methodology 1200 can iterate on a medical device and an implantation path until a medical device/path pair suitable for a medical procedure is determined.

At 1210, analysis to facilitate a recommendation of a medical device and/or a path is performed. The recommendation analysis can include a step 1212 where a medical device is selected. The recommendation analysis can also include a step 1214 where virtual simulation implantation along each candidate path is performed. Furthermore, the recommendation analysis can include a step 1216 where an automatic best fit result is selected. If no valid path is found after step 1216, step 1212 can be performed again and the recommendation analysis process can be repeated. If a valid path is found for the medical device after step 1216, at step 1218 it is determined to proceed to recommend the valid path and the medical device. For example, once an implantation path and a medical device are determined by the methodology 1200, a user device can be provided with an interactive 3D visual sequence. At step 1220, multi-dimensional visualization is performed. The multi-dimensional visualization can include a step 1222 where an interactive 3D visual sequence is provided to a user. The multi-dimensional visualization can include a step 1224 where output is recorded. For example, information associated with the selected implantation path and/or the selected medical device can be recorded for later user (e.g., for use during a 3D printing process, for use during a manufacturing process, for use during clinician reporting, etc.).

Figure 13:
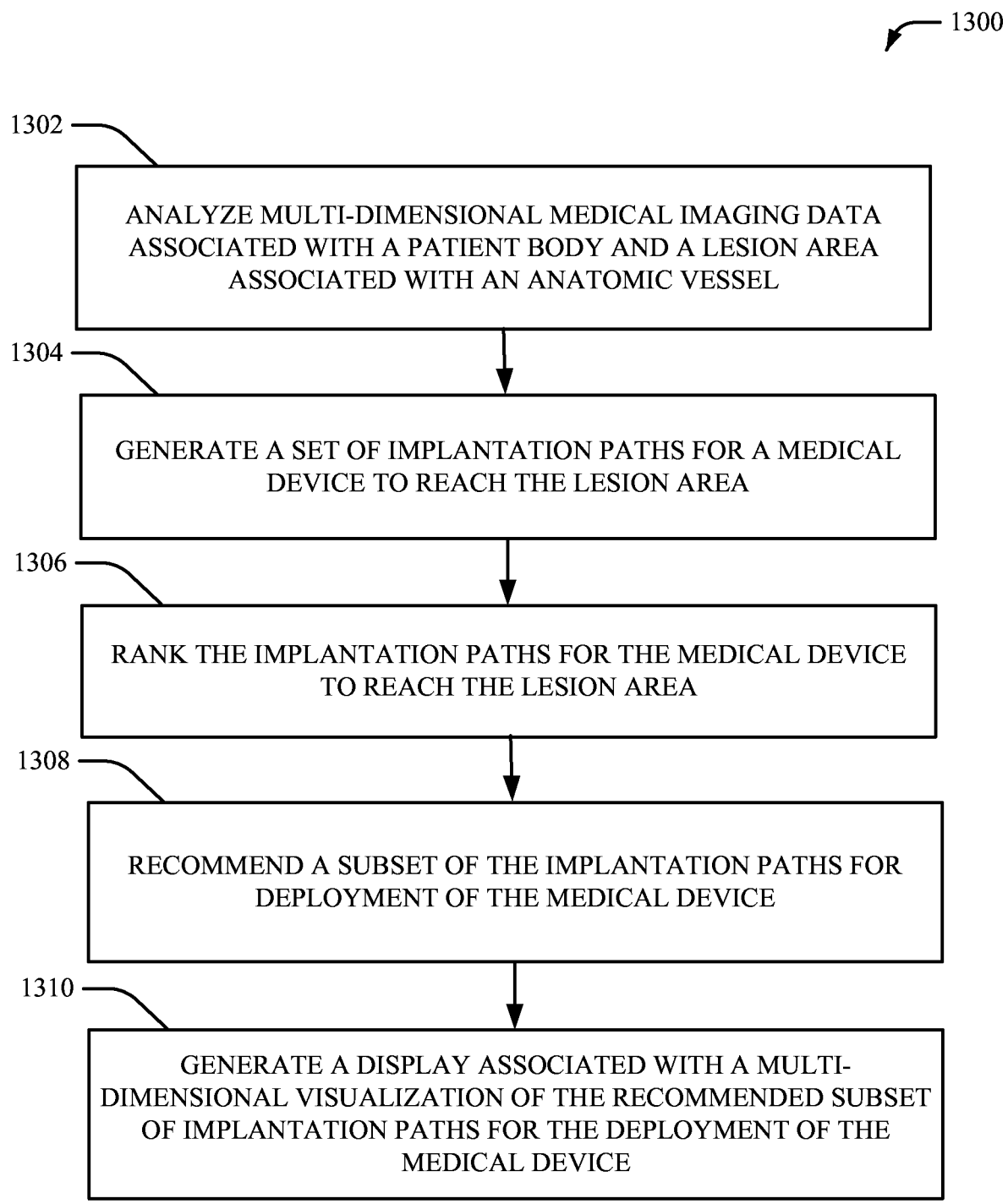
FIG. 13 depicts a flow diagram of an example method for recommending an implantation path for a medical device, in accordance with various aspects and implementations described herein.

Referring to FIG. 13, there illustrated is a methodology 1300 for recommending an implantation path for a medical device, according to an aspect of the subject innovation. As an example, the methodology 1300 can be utilized in various applications, such as, but not limited to, medical device systems, medical imaging systems, medical modeling systems, simulation systems, medical device navigation systems, stent navigation systems, enterprise imaging solution systems, advanced diagnostic tool systems, image management platform systems, care delivery management systems, artificial intelligence systems, machine learning systems, neural network systems, and the like. At 1302, multi-dimensional medical imaging data associated with a patient body and a lesion area associated with an anatomic vessel is analyzed. For example, a portion of 3D medical imaging data associated with an anatomic vessel of a patient body can be analyzed. Furthermore, another portion of the 3D medical imaging data associated with a lesion area of the anatomic vessel can be analyzed. The multi-dimensional medical imaging data can be analyzed based on a segmentation process. For instance, the multi-dimensional medical imaging data can be analyzed by employing one or more segmentation algorithms and/or one or more statistical algorithms. In an aspect, geometric data, texture data and/or mesh data associated with the multi-dimensional medical imaging data can be analyzed. Additionally or alternatively, volumetric features, surface features, density features, geometric features, polygons, vectors, vertices, edges, faces and/or other features identified in the multi-dimensional medical imaging data can be analyzed.

At 1304, a set of implantation paths for a medical device to reach the lesion area is generated. For example, a set of candidate implantation paths for a medical device to traverse an anatomic vessel in order to reach the lesion area can be determined. The set of implantation paths can be generated based on properties and/or characteristics associated with the medical device. Additionally, the set of implantation paths can be generated based on properties and/or characteristics associated with the anatomic vessel. In a non-limiting example, the set of implantation paths can be generated based at least on deformation properties associated with the medical device and/or the anatomic vessel.

At 1306, the implantation paths for the medical device to reach the lesion area are ranked. For example, implantation paths for the medical device can be ranked based on properties associated with the medical device, properties associated with the anatomic vessel and/or a score generated for each candidate implantation path. In an aspect, a higher ranked implantation path can correspond to an implantation path with a higher probability of fitting the anatomic vessel and/or limiting damage to the anatomic vessel. In an aspect, the implantation paths can be ranked by virtually simulating an implantation process associated with each of the implantation paths.

At 1308, a subset of the implantation paths for deployment of the medical device is recommended. For example, at least one implantation path can be recommended for the medical device based on properties associated with the medical device, properties associated with the anatomic vessel and/or a score generated for each candidate implantation path. Furthermore, at least one implantation path can be recommended for the medical device by performing learning to weigh costs and benefits associated with each of the implantation paths to reach the lesion area.

At 1310, a display associated with a multi-dimensional visualization of the recommended subset of implantation paths for the deployment of the medical device is generated. For example, a 3D visualization of the at least one implantation path for the medical device can be presented on a display of a user device. In an aspect, a 3D rendering of the anatomic vessel along with the at least one implantation path and the medical device can be presented on a display of a user device.

Figure 14:
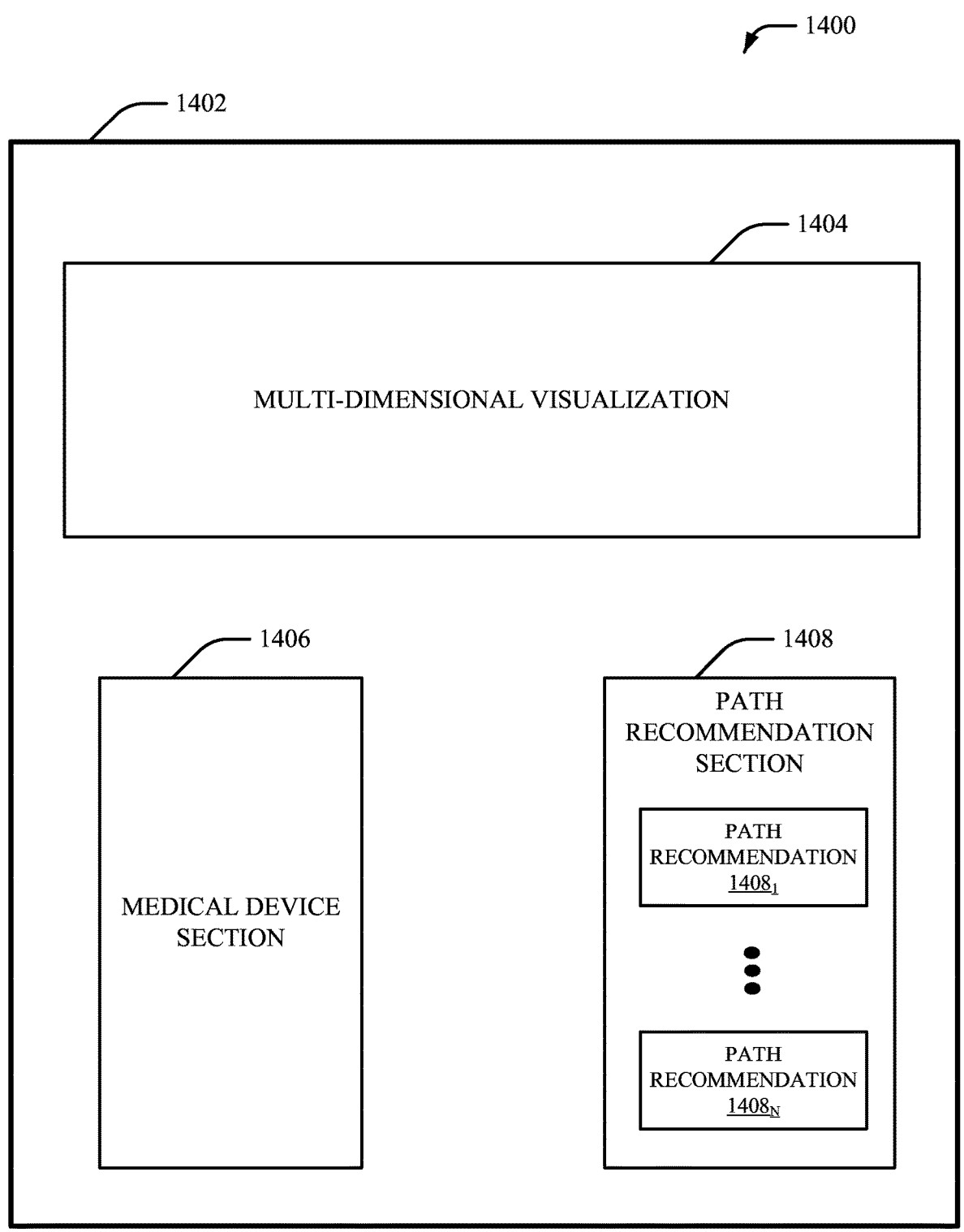
FIG. 14 illustrates an example user interface, in accordance with various aspects and implementations described herein.

Referring to FIG. 14, there is illustrated a non-limiting implementation of a system 1400, in accordance with various aspects and implementations of this disclosure. In an aspect, the system 1400 can be associated with a user device such as, for example, a computing device, a computer, a desktop computer, a laptop computer, a monitor device, a smart device, a smart phone, a mobile device, a handheld device, a tablet, a portable computing device or another type of user device associated with a display. The system 1400 illustrates an example user interface 1402. The user interface 1402 can be a graphical user interface that presents a multi-dimensional visualization 1404 section associated with a recommended set of implantation paths for deployment of a medical device. For example, the multi-dimensional visualization 1404 section of the user interface 1402 can present a multi-dimensional visualization (e.g., a 3D visualization) of a recommended set of implantation paths determined by the path recommendation component 106. The multi-dimensional visualization 1404 section of the user interface 1402 can present an interactive multi-dimensional visual sequence associated with an implantation path from the recommended subset of implantation paths. For example, the multi-dimensional visualization 1404 section of the user interface 1402 can present a multi-dimensional sequence of frames that depict different portions of the implantation path with respect to a medical device and an anatomic vessel. A medical device presented via the multi-dimensional visualization 1404 section of the user interface 1402 can be a 3D rendering of the medical device. Furthermore, an anatomic vessel presented via the multi-dimensional visualization 1404 section of the user interface 1402 can be a 3D rendering of the anatomic vessel. As such, a user can view, analyze and/or interact with a 3D rendering of the medical device as the medical device traverses through a 3D rendering of the anatomic vessel via the recommended subset of implantation paths.

The user interface 1402 can also include a medical device section 1406 associated with information for the medical device. The medical device section 1406 can be presented as a graphical element such as, but not limited to, a notification, a message, an icon, a thumbnail, a dialog box, an interactive tool, a widget or another type of graphical element. The medical device associated with the medical device section 1406 can be selected based on user input or alternatively by the medical device recommendation component 502. Furthermore, the user interface 1402 can include a path recommendation section 1408 that includes a set of path recommendations 1408$_{1-N}$. The path recommendation section 1408 can be presented as a graphical element such as, but not limited to, a notification, a message, an icon, a thumbnail, a dialog box, an interactive tool, a widget or another type of graphical element. Furthermore, the set of path recommendations 1408$_{1-N}$ can be determined by the path recommendation component 106. It is to be appreciated that the user interface 1402 is merely an example. Therefore, the location and/or content of the multi-dimensional visualization 1404, the medical device section 1406 and/or the path recommendation section 1408 can be varied. Furthermore, the user interface 1402 can include other features, content and/or functionalities not shown in FIG. 14.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 15:
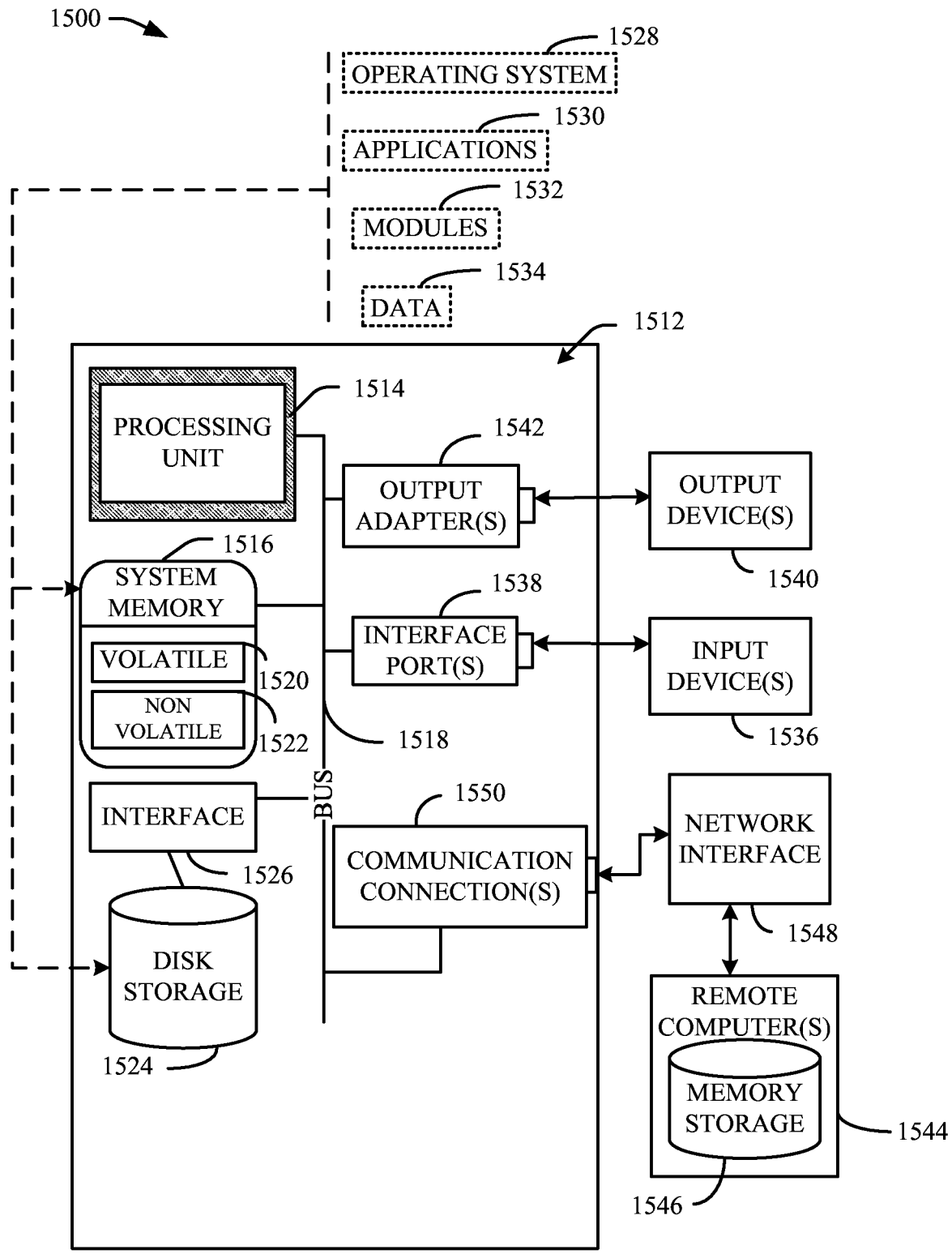
FIG. 15 is a schematic block diagram illustrating a suitable operating environment.
Figure 16:
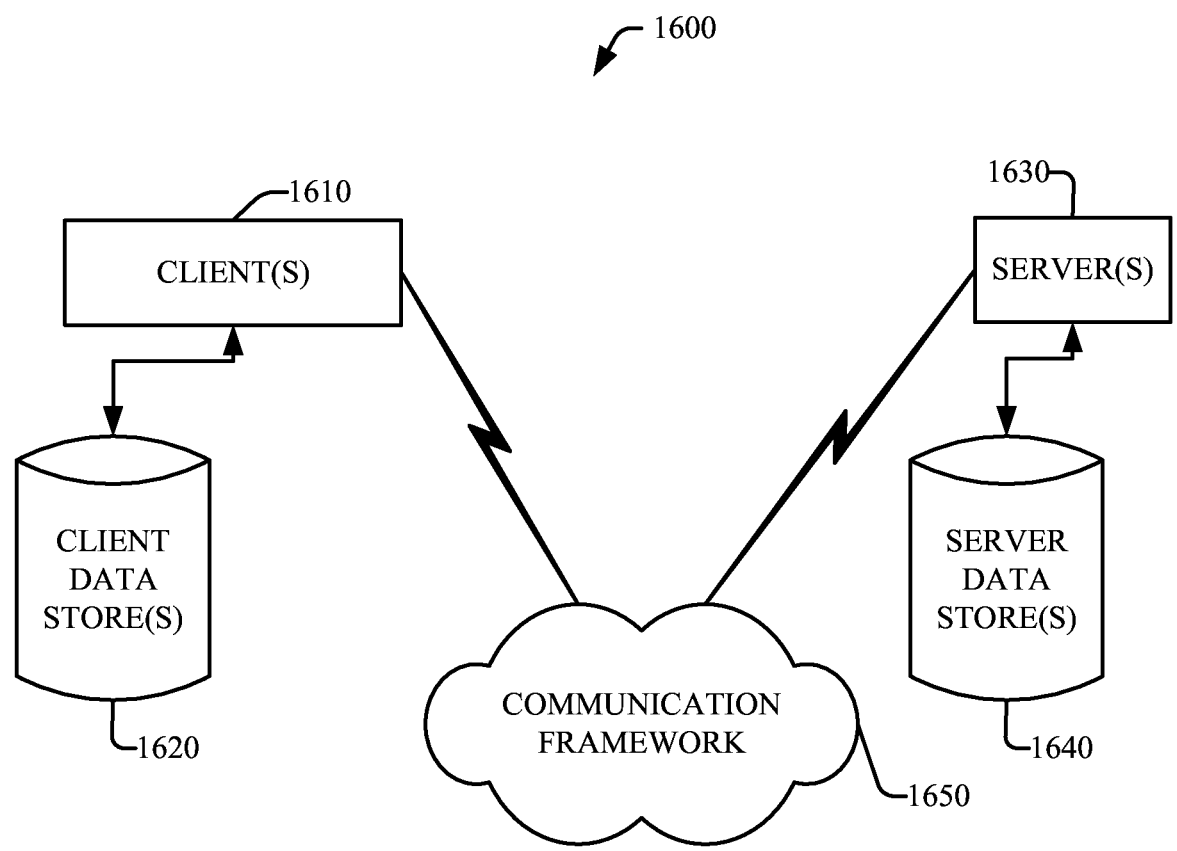
FIG. 16 is a schematic block diagram of a sample-computing environment.

In order to provide a context for the various aspects of the disclosed subject matter, FIGS. 15 and 16 as well as the following discussion are intended to provide a brief, general description of a suitable environment in which the various aspects of the disclosed subject matter may be implemented.

With reference to FIG. 15, a suitable environment 1500 for implementing various aspects of this disclosure includes a computer 1512. The computer 1512 includes a processing unit 1514, a system memory 1516, and a system bus 1518. The system bus 1518 couples system components including, but not limited to, the system memory 1516 to the processing unit 1514. The processing unit 1514 can be any of various available processors. Dual microprocessors and other multiprocessor architectures also can be employed as the processing unit 1514.

The system bus 1518 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1516 includes volatile memory 1520 and nonvolatile memory 1522. The basic input/output system (BIOS), containing the basic routines to transfer information between elements within the computer 1512, such as during start-up, is stored in nonvolatile memory 1522. By way of illustration, and not limitation, nonvolatile memory 1522 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1520 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1512 also includes removable/non-removable, volatile/non-volatile computer storage media. FIG. 15 illustrates, for example, a disk storage 1524. Disk storage 1524 includes, but is not limited to, devices like a magnetic disk drive, floppy disk drive, tape drive, Jaz drive, Zip drive, LS-100 drive, flash memory card, or memory stick. The disk storage 1524 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1524 to the system bus 1518, a removable or non-removable interface is typically used, such as interface 1526.

FIG. 15 also depicts software that acts as an intermediary between users and the basic computer resources described in the suitable operating environment 1500. Such software includes, for example, an operating system 1528. Operating system 1528, which can be stored on disk storage 1524, acts to control and allocate resources of the computer system 1512. System applications 1530 take advantage of the management of resources by operating system 1528 through program modules 1532 and program data 1534, e.g., stored either in system memory 1516 or on disk storage 1524. It is to be appreciated that this disclosure can be implemented with various operating systems or combinations of operating systems.

A user enters commands or information into the computer 1512 through input device(s) 1536. Input devices 1536 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1514 through the system bus 1518 via interface port(s) 1538. Interface port(s) 1538 include, for example, a serial port, a parallel port, a game port, and a universal serial bus (USB). Output device(s) 1540 use some of the same type of ports as input device(s) 1536. Thus, for example, a USB port may be used to provide input to computer 1512, and to output information from computer 1512 to an output device 1540. Output adapter 1542 is provided to illustrate that there are some output devices 1540 like monitors, speakers, and printers, among other output devices 1540, which require special adapters. The output adapters 1542 include, by way of illustration and not limitation, video and sound cards that provide a means of connection between the output device 1540 and the system bus 1518. It should be noted that other devices and/or systems of devices provide both input and output capabilities such as remote computer(s) 1544.

Computer 1512 can operate in a networked environment using logical connections to one or more remote computers, such as remote computer(s) 1544. The remote computer(s) 1544 can be a personal computer, a server, a router, a network PC, a workstation, a microprocessor based appliance, a peer device or other common network node and the like, and typically includes many or all of the elements described relative to computer 1512. For purposes of brevity, only a memory storage device 1546 is illustrated with remote computer(s) 1544. Remote computer(s) 1544 is logically connected to computer 1512 through a network interface 1548 and then physically connected via communication connection 1550. Network interface 1548 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1550 refers to the hardware/software employed to connect the network interface 1548 to the bus 1518. While communication connection 1550 is shown for illustrative clarity inside computer 1512, it can also be external to computer 1512. The hardware/software necessary for connection to the network interface 1548 includes, for exemplary purposes only, internal and external technologies such as, modems including regular telephone grade modems, cable modems and DSL modems, ISDN adapters, and Ethernet cards.

FIG. 16 is a schematic block diagram of a sample-computing environment 1600 with which the subject matter of this disclosure can interact. The system 1600 includes one or more client(s) 1610. The client(s) 1610 can be hardware and/or software (e.g., threads, processes, computing devices). The system 1600 also includes one or more server(s) 1630. Thus, system 1600 can correspond to a two-tier client server model or a multi-tier model (e.g., client, middle tier server, data server), amongst other models. The server(s) 1630 can also be hardware and/or software (e.g., threads, processes, computing devices). The servers 1630 can house threads to perform transformations by employing this disclosure, for example. One possible communication between a client 1610 and a server 1630 may be in the form of a data packet transmitted between two or more computer processes.

The system 1600 includes a communication framework 1650 that can be employed to facilitate communications between the client(s) 1610 and the server(s) 1630. The client(s) 1610 are operatively connected to one or more client data store(s) 1620 that can be employed to store information local to the client(s) 1610. Similarly, the server(s) 1630 are operatively connected to one or more server data store(s) 1640 that can be employed to store information local to the servers 1630.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A medical device implantation path assessment system, comprising:
   a memory that stores computer executable components;
   a processor that executes the computer executable components stored in the memory, the computer executable components comprising:
   a path assessment component that analyzes mesh data included in three-dimensional medical imaging data regarding a patient body and a lesion area, wherein the path assessment component generates a set of candidate paths to reach the lesion area for deployment of a medical device based on a segmentation process with respect to the mesh data included in the three-dimensional medical imaging data;
   a recommendation component that selects a path from the set of candidate paths for the deployment of the medical device based on respective ranks assigned to candidate paths of the set of candidate paths, wherein the respective ranks are determined for the candidate paths based on respective rigid deformation values for the medical device and the candidate paths of the set of candidate paths; and
   a visualization component that generates a multi-dimensional visualization of the path selected by the recommendation component for the deployment of the medical device.

2. The medical device implantation path assessment system of claim 1, wherein the visualization component generates an interactive multi-dimensional visual sequence associated with the path selected by the recommendation component.

3. The medical device implantation path assessment system of claim 1, wherein the medical device is a stent.

4. The medical device implantation path assessment system of claim 1, wherein the three-dimensional medical imaging data comprises geometric data and texture data regarding the patient body.

5. The medical device implantation path assessment system of claim 1, wherein the recommendation component comprises an artificial intelligence component that performs a probabilistic based utility analysis that weighs costs and benefits associated with each candidate path from the set of candidate paths to reach the lesion area.

6. The medical device implantation path assessment system of claim 1, further comprising a medical device recommendation component that, based at least in part on analyses performed by the path assessment component analyses, recommends a subset of available medical devices to be deployed.

7. The medical device implantation path assessment system of claim 6, wherein the medical device recommendation component selects the medical device based in part on mechanical properties associated with the medical device to fit curvature of an anatomic vessel associated with the lesion area or to fit a cross-sectional area of the anatomic vessel.

8. The medical device implantation path assessment system of claim 1, further comprising a modeling component that generates, based at least in part on analyses performed by the path assessment component, a model for the medical device to be deployed to the lesion area.

9. The medical device implantation path assessment system of claim 8, wherein the modeling component generates a three-dimensional printing model of the medical device.

10. The medical device implantation path assessment system of claim 1, further comprising an archiving component that stores path assessments, rankings, recommendations, and visualizations.

11. A method, comprising:
   analyzing, by a system comprising a processor, mesh data included in three-dimensional medical imaging data associated with a patient body and a lesion area related to an anatomic vessel, comprising performing a segmentation process with respect to the mesh data;

generating, by the system, a set of candidate implantation paths for a medical device to reach the lesion area based on the segmentation process;

ranking, by the system, the set of candidate implantation paths for the medical device to reach the lesion area based on a respective number of turns for deployment of the medical device through candidate implantations paths of the set of candidate implantation paths;

recommending, by the system, an implantation path from the set of candidate implantation paths for the deployment of the medical device based on the ranking; and generating, by the system, a display associated with a multi-dimensional visualization of the implantation path for the deployment of the medical device.

12. The method of claim 11, wherein the recommending comprises performing learning to weigh respective costs and benefits associated with each implantation paths of the set of candidate implantation paths to reach the lesion area.

13. The method of claim 11, further comprising recommending, by the system, a subset of available medical devices to be deployed to the lesion area.

14. The method of claim 11, further comprising selecting, by the system, the medical device based in part on properties associated with the medical device and the anatomic vessel.

15. The method of claim 11, further comprising generating, by the system, a model for the medical device to be deployed to the lesion area.

16. The method of claim 11, further comprising storing, by the system, data associated with the implantation path and the multi-dimensional visualization.

17. A computer readable storage device comprising instructions that, in response to execution, cause a system comprising a processor to perform operations, comprising:

segmenting mesh data included in a three-dimensional mesh model of an anatomic vessel and a lesion area associated with the anatomic vessel;

generating, based on the segmenting of the mesh data included in the three-dimensional mesh model, a set of candidate implantation paths for a medical device to reach the lesion area;

ranking the set of candidate implantation paths for the medical device to reach the lesion area based on a flexibility of the medical device and respective capabilities of candidate implantation paths of the set of candidate implantation paths to accommodate the medical device;

selecting, from the set of candidate implantation paths, an implantation path for deployment of the medical device based on the ranking; and generating a display associated with a three-dimensional rendering of the implantation path for the deployment of the medical device.

18. The computer readable storage device of claim 17, wherein the segmenting comprises segmenting a portion of the three-dimensional mesh model associated with the anatomic vessel and segmenting another portion of the three-dimensional mesh model associated with the lesion area.

19. The computer readable storage device of claim 17, wherein the ranking comprises ranking the set of candidate implantation paths based on properties associated with the anatomic vessel and other properties associated with the medical device.

20. The computer readable storage device of claim 17, wherein the ranking comprises virtually simulating an implantation process associated with the set of candidate implantation paths.

* * * * *